US008798936B2

(12) United States Patent
Bauer et al.

(10) Patent No.: US 8,798,936 B2
(45) Date of Patent: Aug. 5, 2014

(54) METHODS AND SYSTEMS FOR DATA ANALYSIS USING THE BURROWS WHEELER TRANSFORM

(75) Inventors: Markus J. Bauer, Mariapfarr (AT); Anthony James Cox, Nr Saffron Walden (GB); Giovanna Rosone, Palermo (IT); Dirk Evers, Arkesden (GB)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 13/459,968

(22) Filed: Apr. 30, 2012

(65) Prior Publication Data

US 2012/0330567 A1   Dec. 27, 2012

Related U.S. Application Data

(60) Provisional application No. 61/499,587, filed on Jun. 21, 2011.

(51) Int. Cl.
*G01N 33/48*   (2006.01)
*G06F 5/00*   (2006.01)

(52) U.S. Cl.
USPC .............................................. 702/19; 710/68

(58) Field of Classification Search
None
See application file for complete search history.

(56) References Cited

U.S. PATENT DOCUMENTS

| | | | |
|---|---|---|---|
| 6,199,064 B1 | 3/2001 | Schindler |
| 7,028,042 B2 | 4/2006 | Rissanen |
| 7,734,671 B1 | 6/2010 | Ferguson |
| 7,881,544 B2 | 2/2011 | Bashyam et al. |

FOREIGN PATENT DOCUMENTS

EP   1057269   2/1999

OTHER PUBLICATIONS

Le et al. "Fast and accurate short read alignment with Burrows-Wheeler transform", Bioinformatics, vol. 25 (2009) pp. 1754-1760.*
McKenna et al. "The Genome Analysis Toolkit: A MapReduce framework for analyzing next-generation DNA sequencing data," vol. 20 (2010) pp. 1297-1303.*
Bauer, Markus J., Anthony J. Cox, and Giovanna Rosone. "Lightweight BWT construction for very large string collections." Combinatorial Pattern Matching. Springer Berlin Heidelberg, Sep. 2011.*
Bauer, Markus J., Anthony J. Cox, and Giovanna Rosone. "Lightweight BWT construction for very large string collections." Incontro PRIN, Sep. 2011.*
Burrows and Wheeler, "A block-sorting lossless data compression algorithm", SRC Research Report 124, Digital Systems Research Center, pp. 1-18, 1994.
Chen et al., "DNACompress: fast and effective DNA sequence compression" Bioinformatics 18:1696-1698, 2002.
Ferragina, Paolo et al., "Lightweight Data Indexing and Compression in External Memory", 2012, Algorithmica 63:707-730.
Ferragina, Paolo , "The FM-Index: A Compressed Full-Text Index Based on the BWT", DIMACAS, Aug. 19-20, 2004, 15-16.
Ferragina, Paolo et al., "Opportunistic Data Structures with Applications", Foundations of Computer Science Proceedings 41st Annual Symposium, 2000, 390-398.
Ferragina and Manzini, "Indexing compressed text" J ACM 52:552-581, 2005.
Flicek and Birney, "Sense from sequence reads: methods for alignment and assembly" Nat. Meth. 6:6S-12S, 2009.
Fischer, Johannes , "Space-Efficient String Mining under Frequency Constraints", In Proc. Eighth IEEE International Conference on Data Mining, 2008, 11 pages.
Fritz et al., "Efficient storage of high throughput DNA sequencing data using reference-based compression" Genome Research 21:734-740, 2011.
Giancarlo, Raffaele et al., "Textual data compression in computational biology: a synopsis", Bioinformatics, vol. 25 No. 13 2009, pp. 1575-1586.
Healy, John et al., "Annotating Large Genomes With Exact Word Matches", Genome Res. 2003 13: 2306-2315.
Kozanitis et al., "Compressing genomic sequence fragments using Slimgene" In Recomb. vol. 6044 of LNCS p. 310-325, 2010.
Li and Durbin, "Fast and accurate long-read alignment with Burrows-Wheeler transform", vol. 26 No. 5 2010, pp. 589-595.
Li and Durbin, "Fast and accurate short read alignment with Burrows-Wheeler transform" Bioinformatics 25:1754-1760, 2009.
Mantaci et al, "An extension of the Burrows Wheeler Transform and application to sequence comparison and data compression" In CPM 2005 vol. 3537 of LNCS p. 178-179, 2005.
Mantaci, S. et al., "A New Combinatorial Approach to Sequence", Theory Comput Syst (2008) 42: 411-429.
Mantaci, S. et al., "An extension of the Burrows-Wheeler Transform", Theoretical Computer Science 387 (2007) 298-312.
Pereira, Pedro et al., "Fast Discovery of Statistically Interesting Words", 2008, University Porto Technical Report, 10 pages.
Puglisi et al., "A taxonomy of suffix array construction algorithms" ACM Comp Sur 39, 1-39, 2007.
Siren, "Compressed suffix arrays for massive data" In: SPIRE vol. 5721 of LNCS pp. 63-74, 2009.
Weese, David et al., "Efficient String Mining Under Constraints via the Deferred Frequency Index", 2008, Proceedings from Industrial Conference on Data Mining, 8th Annual, pp. 1-15.
Yanovsky, ReCoil—an algorithm for compression of extremely large datasets of DNA data Alg Mol Biol 6:23, 2011.
Ziv, Jacob et al., "A Universal Algorithm for Sequential Data Compression", IEEE Transactions on Information Theory, vol. IT-23, No. 3, May 1977, 337-343.

* cited by examiner

*Primary Examiner* — Anna Skibinsky
(74) *Attorney, Agent, or Firm* — Victor Huang

(57) ABSTRACT

The present disclosure provides computer implemented methods and systems for analyzing datasets, such as large data sets output from nucleic acid sequencing technologies. In particular, the present disclosure provides for data analysis comprising computing the BWT of a collection of strings in an incremental, character by character, manner. The present disclosure also provides compression boosting strategies resulting in a BWT of a reordered collection of data that is more compressible by second stage compression methods compared to non-reordered computational analysis.

80 Claims, 6 Drawing Sheets

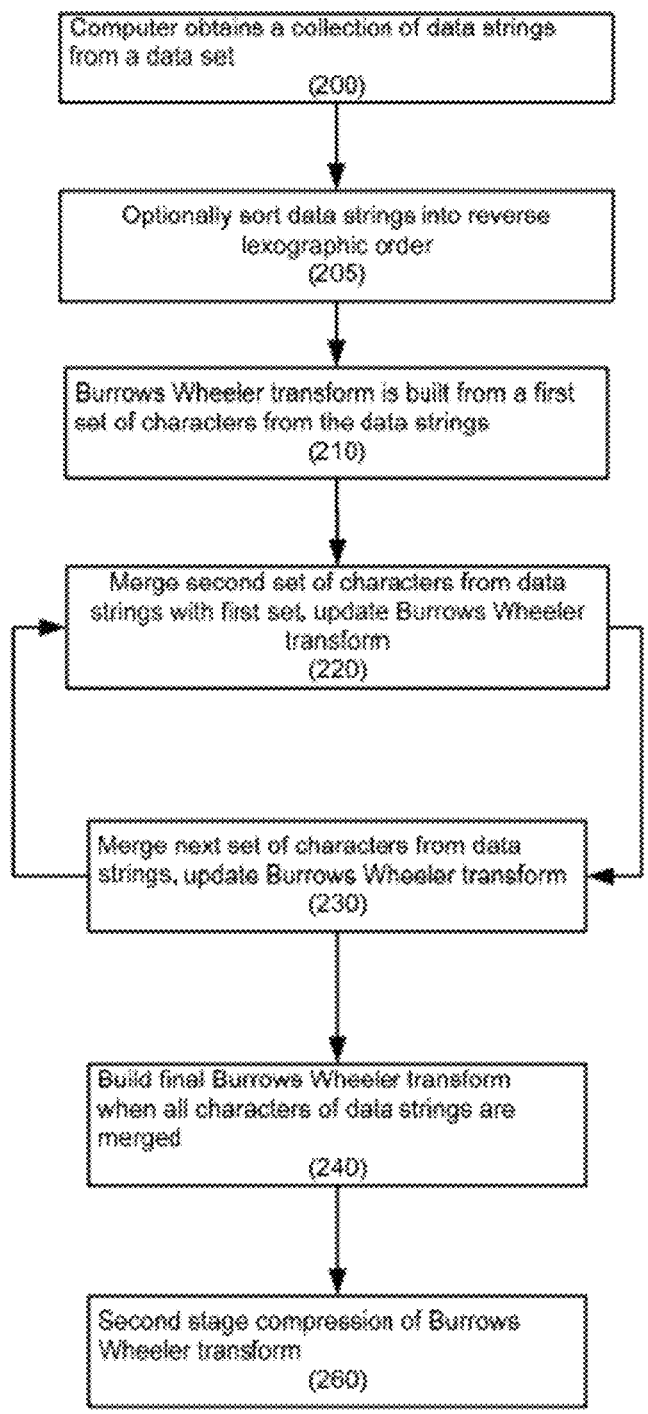

FIGURE 4

Figure 1:
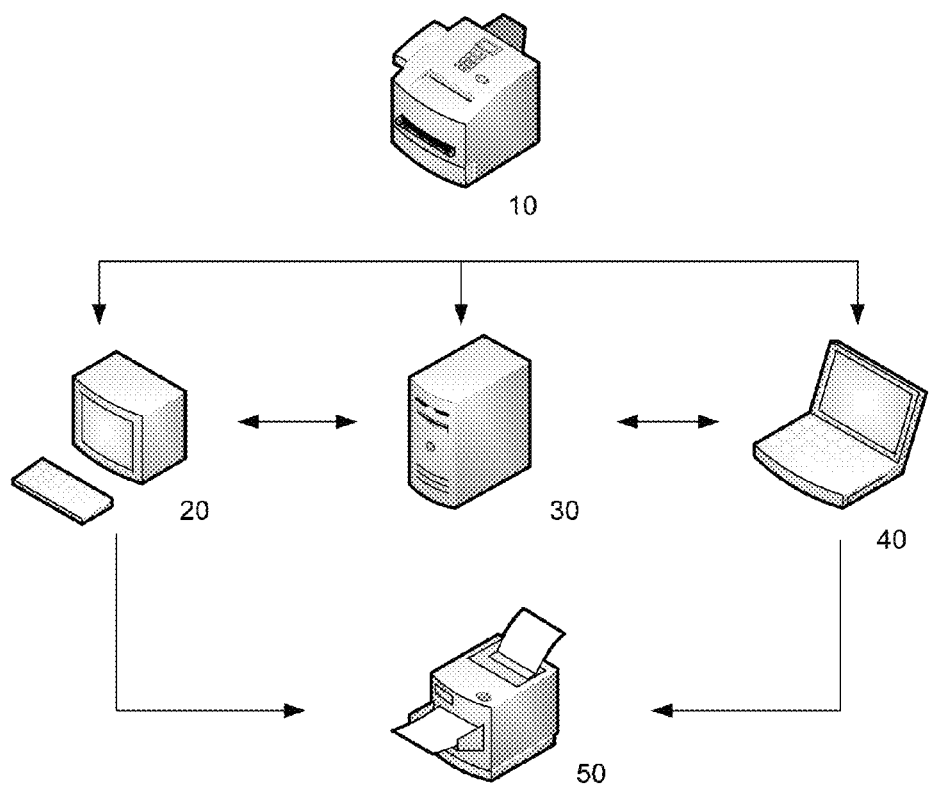

| B(0) | SAP(0) | suffixes | $B_{SAP}(0)$ |
|---|---|---|---|
| T | 0 | $S_1$ | T |
| T | 1 | $S_2$ | T |
| T | 1 | $S_3$ | T |
| T | 1 | $S_4$ | T |
| B(1) | SAP(1) | suffixes | $B_{SAP}(1)$ |
| T | 0 | $ACCACTS_2$ | T |
| G | 0 | $ACCTS_1$ | G |
| T | 1 | $ACCTS_3$ | G |
| G | 1 | $ACCTS_4$ | T |
| C | 0 | $ACTS_3$ | C |
| T | 0 | $AGACCTS_1$ | G |
| G | 1 | $AGACCTS_4$ | T |
| G | 0 | $ATACCTS_2$ | G |
| B(2) | SAP(2) | suffixes | $B_{SAP}(2)$ |
| C | 0 | $CACTS_3$ | C |
| A | 0 | $CCACTS_2$ | A |
| A | 1 | $CCTS_1$ | A |
| A | 1 | $CCTS_3$ | A |
| A | 1 | $CCTS_4$ | A |
| C | 0 | $CTS_1$ | C |
| C | 1 | $CTS_2$ | C |
| A | 1 | $CTS_3$ | C |
| A | 1 | $CTS_4$ | C |
| B(3) | SAP(3) | suffixes | $B_{SAP}(3)$ |
| A | 0 | $GACCTS_1$ | A |
| A | 1 | $GACCTS_4$ | A |
| $S_4$ | 0 | $GAGACCTS_4$ | $S_4$ |
| $S_2$ | 0 | $GATACCTS_2$ | $S_2$ |
| B(4) | SAP(4) | suffixes | $B_{SAP}(4)$ |
| C | 0 | $TS_1$ | C |
| C | 1 | $TS_2$ | C |
| C | 1 | $TS_3$ | C |
| C | 1 | $TS_4$ | C |
| $S_3$ | 0 | $TACCACTS_3$ | $S_3$ |
| A | 0 | $TACCTS_2$ | A |
| $S_1$ | 0 | $TAGACCTS_1$ | $S_1$ |

METHODS AND SYSTEMS FOR DATA ANALYSIS USING THE BURROWS WHEELER TRANSFORM

This patent application claims priority to U.S. Patent Application Ser. No. 61/499, 587 filed Jun. 21, 2011 which is incorporated herein by reference in its entirety.

BACKGROUND

Data compression is a process that encodes information into a more compact form. Data compression is an important and well-studied topic with clear economic benefits: compressed data is cheaper to store, either on a computer's hard drive or in a computer's random access memory (RAM), and requires less bandwidth to transmit.

As well as the level of compression achieved, the computational overheads (such as the amount of CPU time used or the amount of available RAM needed) of both compressing and decompressing the data must also be taken into account in choosing an appropriate compression strategy. In some applications (for example in compressing high resolution images for display on a web page), a lossy compression approach may be appropriate, allowing greater compression to be achieved at the expense of some loss of information during the compression process. In other applications, it is important that a perfect copy of the original data can be extracted from the compressed data. A lossless compression strategy is the appropriate choice for such cases.

For many applications of data compression, such as a variety used in biological sequence analysis, it is important that the original data be retrievable in its original, uncompressed form. Compression of data, and its reversal, becomes a trade-off of numerous factors, such as degree of compression versus the computational resources required to compress and uncompress the data and the time in which to do so.

Technology for determining the sequence of an organism's DNA has progressed dramatically since its genesis back in the 1970s when DNA was first sequenced (Maxam-Gilbert sequencing). With the development of dye-terminator based sequencing (Sanger sequencing) and related automated technologies, the field of nucleic acid sequencing took a giant step forward. The advent of dye based technologies and instrumentation and automated sequencing methods required development of related software and data processes to deal with the generated data.

Much of the early work on the compression of DNA sequences was motivated by the notion that the compressibility of a DNA sequence could serve as a measure of its information content and hence as a tool for sequence analysis. This concept was applied to topics such as feature detection in genomes and alignment free methods of sequence comparison, a comprehensive review of the field up to 2009 is found, for example, in Giancarlo et al (2009, Bioinformatics 25:1575-1586, incorporated herein by reference in its entirety). However, the exponential growth in the size of a nucleotide sequence database is a reason to be interested in compression for its own sake. The recent and rapid evolution of DNA sequencing technology has given the topic more practical relevance than ever.

The high demand for high-throughput, low cost nucleic acid sequencing methods and systems is driving the state of the art, leading to technologies that parallelize the sequencing process, producing very large amounts of sequence data at one time. Fueled by the commercial availability of a variety of high throughput sequencing platforms, current large scale sequencing projects generate reams of data, in the gigabyte and terabyte range.

Computer systems and data processing software for data analysis associated with current sequencing technologies have advanced considerably. Programs for compressing data that applies to generated sequence data, indexing the data, analyzing the data, and storing the data are available. However, computational analysis for large data sets, such as those generated by current and future sequencing technologies where data in the terabyte range is conceivable, is still a confounding issue as the amount of generated data is so large that analyzing and interpreting it presents a bottleneck for many investigators. Further, current computational sequence analysis requires an enormous amount of computer capacity and is not easily practiced on a typical desktop personal computer or laptop. As such, what are needed are methods and systems for computational analysis that can analyze very large datasets in a time efficient manner and that are easily managed on a typical desktop or laptop computer system, providing both efficiencies in both computer resource usage and time.

SUMMARY

The Burrows-Wheeler transform (BWT) is a useful method for transforming information into a more compressible form. However, the computational demands of creating the BWT of a large dataset, such as datasets of gigabyte and terabyte proportion, have been an impediment for some applications.

For example, data sets output from sequencing methodologies can require large amounts of computer memory for performing data compression and the data compression computations themselves can be time inefficient. The methods disclosed herein overcome these hurdles by providing new ways for computing the BWT from a large dataset, for example a sequence dataset, which decreases the amount of computer space needed to perform the computations in conjunction with decreasing the time from data input to sequence output (e.g., increasing time efficiency). It is advantageous to improve and increase computational efficiencies when dealing with large datasets as such improvements necessarily go hand in hand with technological advances in those areas of application which produce large data sets, like sequencing technologies. In other words, to move forward in terms of advancing and evolving the realms of diagnsostic, prognositic, therapeutic and research related technologies there should also be concurrent advances to deal with the enormous amount of data produced by these constantly advancing technologies; the present application provides methods and systems to do just that.

The present disclosure describes methods and systems for computing the Burrows Wheeler transform of a collection of data strings by building the BWT in a character by character cumulative manner along a collection of data strings. The methods and systems can be used on any length data strings from a variety of data sources, such as those generated during sequencing (e.g. nucleic acids, amino acids), language texts (e.g. words, phrases, and sentences), image derived (e.g. pixel maps or grids), and the like. The datasets can be datasets as found on, for example, a computer readable storage medium, or datasets can be those generated live or in real time, such as while an event or assay is in progress. The methods and systems described herein can further accommodate the addition and/or removal of one or more data strings in a dynamic fashion.

The present disclosure also describes methods and systems for reordering the strings in the collection (referred to herein as compression boosting methods), methods which can be performed concurrently (in some embodiments) with the BWT build, such that the resulting BWT is more compressible by second stage compression strategies than would be the case if the original ordering of the strings in the collection was retained.

Computer implemented methods and systems as described herein can be performed on any size dataset, but are especially favorable for computing the BWT of large data sets, such as in the megabyte, gigabyte and terabyte ranges and larger. Methods can be performed in a computer browser, on-demand, on-line, across multiple genomes, with alignment parameters of choice. Described herein are algorithms for use in computer implemented methods and systems that perform the BWT on a collection of strings and increase data compression capabilities while decreasing the demands on computer resources and increasing time efficiencies.

In some embodiments, the present disclosure provides computer implemented methods for determining the Burrows Wheeler transform of a data set comprising obtaining a collection of data strings from a dataset, wherein said data strings comprise a plurality of characters, calculating a Burrows Wheeler transform on a first collection of characters, wherein the first collection of characters comprises a first character from each of said data strings, merging a second collection of characters with the first collection of characters to form a merged collection of characters, wherein the second collection of characters comprises a second character from each of the data strings; and augmenting the Burrows Wheeler transform from the merged first and second collection of characters, thereby determining the Burrows Wheeler transform of the data set. In some embodiments, a data set obtained in practicing a computer implemented method is a biopolymer sequence data set. In some embodiments, a biopolymer sequence data set comprises nucleic acid or amino acid sequence data. In some embodiments a data set comprises nucleic acid sequences from a plurality of organisms. In other embodiments, a data set comprises language text data. In some embodiments, a data set for use in computer implemented methods is obtained from a computer storage medium. In other embodiments, a data set is obtained from a computer in real time such as while a data set is being generated. In some embodiments, a collection of data strings is one data string, whereas in other embodiments a collection of data strings is a plurality of data strings, or two or more data strings. In some embodiments, a collection of data strings for use in computer implemented methods is comprised of a collection of characters from the list comprising nucleotides, amino acids, words, sentences and phrases. In some embodiments a first character from each data string is adjacent to a respective second character from each data string. In some embodiments a first character from a data string is located positionally right of a second character from a data string, and wherein a first and second character are merged in a right to left manner. In some embodiments, a third collection of characters from each data string is merged with the first and second collection of characters, wherein the third collection of characters comprises a third character from each of the data strings and wherein the third character from each of the data strings is located adjacent to the second character from each of the data strings. In some embodiments, results of performing a computer implemented method are output, for example to one or more of a graphic user interface, a printer or a computer readable storage medium. In some embodiments, results output to a computer readable medium are independent of the size of the data set. In some embodiments a second data set is added to the first data set for practicing computer implemented methods as described herein, wherein a collection of data strings comprising a plurality of characters is obtained from second data set, merging the collection of strings from the second data set with the collection of strings from the first data set and incrementally building or augmenting the BWT thereby determining the BWT from the combined first and second data sets. Conversely, one or more of a collection of datasets could be removed from said computer implemented method. In some embodiments, prior to or simultaneous with determining the BWT of a dataset, the data is reordered. In some embodiments, the reordering of the data set is performed prior to determining the BWT by reverse lexicographic ordering. In other embodiments, the reordering of a data set is performed simultaneously with building the BWT by same as previous ordering.

In some embodiments, the present disclosure provides a computer implemented method for determining the sequence of a nucleic acid comprising obtaining a collection of data strings from a nucleic acid sequence dataset wherein the data strings comprise a plurality of characters, calculating a Burrows Wheeler transform on a first collection of characters, wherein the first collection of characters comprises a first character from each of the data strings, merging a second collection of characters with the first collection of characters to form a merged collection of characters, wherein the second collection of characters comprises a second character from each of the data strings, and augmenting the Burrows Wheeler transform from the merged first and second collection of characters, thereby determining the Burrows Wheeler transform of the nucleic acid. In some embodiments, a nucleic acid sequence comprises DNA or RNA sequences. In some embodiments, a nucleic acid sequence comprises nucleic acid sequences from a plurality of organisms. In some embodiments, a sequence data set is obtained from a computer storage medium whereas in other embodiments a sequence data set is obtained from a computer in real time, for example while the data is being generated. In some embodiments, a collection of data strings for use in computer implemented methods is one data string whereas in other embodiments a collection of data strings is a plurality of data strings, for example two or more data strings. In some embodiments, a data string comprises a collection of characters, wherein the characters are one or more characters from the list comprising A, T, C, G, U and N. In some embodiments, a third collection of characters from sequence data strings are merged with the first and third collection of characters, wherein the third collection of characters comprises a third character from each sequence data string and wherein the third character from each sequence data string is located adjacent to the second character from each of the sequence data strings or positionally left of the second character from each of the sequence data strings. In some embodiments, results from determining the nucleic acid sequence by practicing the computer implemented methods comprises outputting the results, such as to one or more of a graphic user interface, a printer or a computer readable storage medium. In some embodiments, the results output to a computer readable medium are independent of the size of a collection of sequence data sets.

In some embodiments, the present disclosure provides a system for determining the Burrows Wheeler transform of a data set comprising a processor, a memory coupled with the processor, the memory storing a plurality of instrument instructions wherein the instructions direct the processor to perform a plurality of logical steps when implemented by the processor, the logical steps comprising obtaining a collection of data strings from a dataset wherein the data strings comprise a plurality of characters, calculating a Burrows Wheeler transform on a first collection of characters, wherein the first collection of characters comprises a first character from each of the data strings, merging a second collection of characters with the first collection of characters to form a merged collection of characters, wherein the second collection of characters comprises a second character from each of the data strings, and augmenting the Burrows Wheeler transform from the merged first and second collection of characters, thereby determining the Burrows Wheeler transform of a data set. In some embodiments, a data set for use in a system as described herein is a biopolymer sequence data set, such as a nucleic acid or amino acid sequence data set. In some embodiments, the data set comprises nucleic acid sequences from a plurality of organisms or language text data. In some embodiments, a system as described herein obtains a data set from a computer storage medium whereas in other embodiments a system obtains a data set from a computer in real time, such as while the data is being generated. In some embodiments, a collection of data strings for use with a system is one data string, whereas in other embodiments a collection of data strings is a plurality of data strings. In some embodiments, a collection of characters that makes up a data string for use in a system described herein are characters from the list comprising nucleotides, amino acids, words, sentences and phrases. In some embodiments, a first character from each of the data strings is adjacent to the respective second character from each of the data strings, whereas in other embodiments a first character from each of the data strings is located positionally right of a second character from each of the data strings, and wherein the characters are merging proceeding in a right to left manner. In some embodiments, at least a third collection of characters for each of the data strings is merged with the preceding collections of characters, wherein the third character from each of the data strings is located adjacent to the second character from each of the data strings, or is located positionally left of the second character from each of the data strings. In some embodiments, a system described herein further outputs a result of determining the Burrows Wheeler transform, for example to one or more of a graphic user interface, a printer or a computer readable storage media. In some embodiments, when a result is output to a computer readable medium the result is independent of the size of the data set. In some embodiments, a system described herein further comprises the addition and/or removal of a data set from determining the Burrows Wheeler transform. In some embodiments, prior to or simultaneous with determining the BWT of a nucleic acid dataset, the data is reordered. In some embodiments, the reordering of the data set is performed prior to determining the BWT by reverse lexicographic ordering. In other embodiments, the reordering of the data set is performed simultaneously with building the BWT by same as previous ordering.

FIGURES

FIG. 1 illustrates exemplary computer hardware communication systems for practicing embodiments as described herein.

FIG. 2 illustrates embodiments of computer implemented methods as described herein. The BWT can be built on a data set either with or without reordering of the data prior to second stage compression methods; A) optional reordering of data using reverse lexographic order method (RLO), and B) optional reordering of data using same as previous method (SAP).

Figure 3:
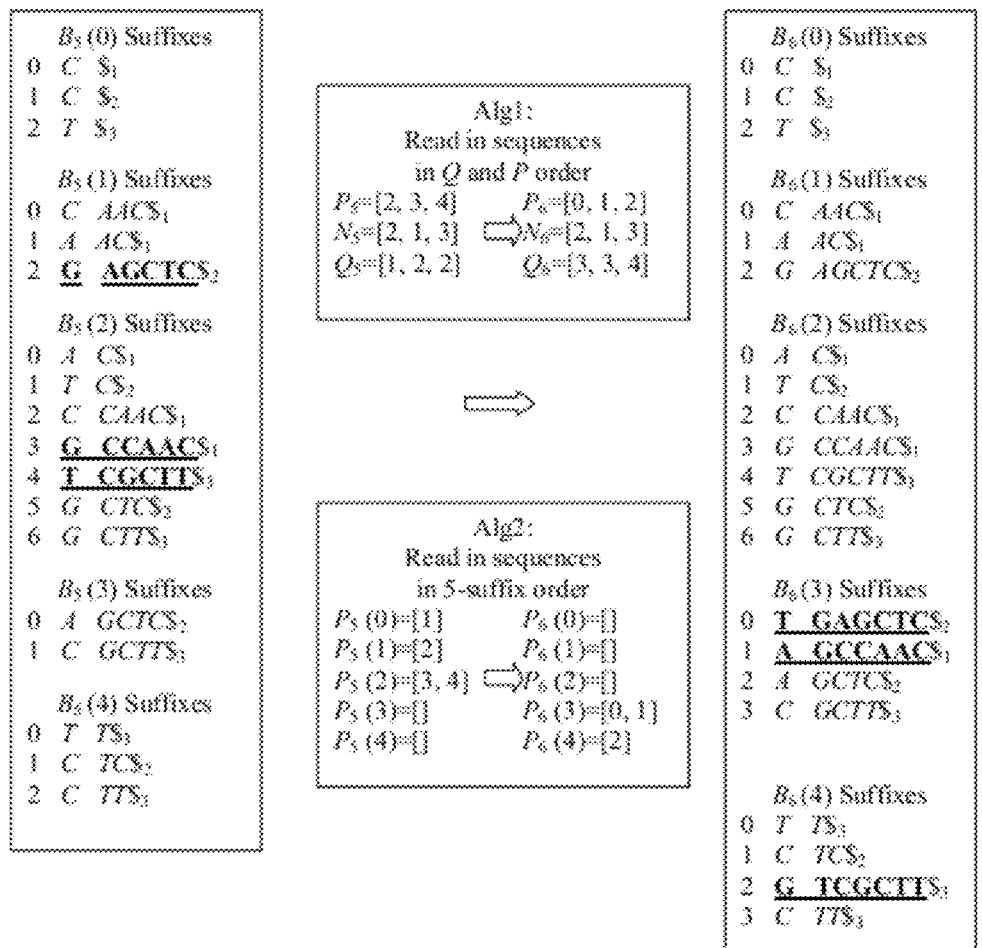

FIG. 3 is exemplary of iteration 6 of the computation of the BWT of the collection S={AGCCAAC, TGAGCTC, GTCGCTT} on the alphabet {A, C, G, T}. The two columns represent the partial BWT before and after the iteration and, in between is seen the auxiliary data stored by the two variants of the algorithm changes during the iteration. The positions of the new symbols corresponding to the 6-suffixes (shown in bold on the right; T GAGCTC, A GCCAAC, G TCGCTT) were computed from the positions of the 5-suffixes (in bold on the left; G AGCTC, G CCAAC, T CGCTT), which were retained in the arrays P after the previous iteration. For clarity, distinct subscripts are given to the end markers of each of the sequences in the collection.

FIG. 4 is exemplary of the implicit first stage sorting compression-boosting strategy embodiment disclosed herein. Columns, from left to right, are the BWT B(n) of the collection S={TAGACCT, GATACCT, TACCACT, GAGACCT}, the SAP bit SAP (n) associated with each symbol, the suffix (suffixes) associated with each symbol and the BWT of the collection {TAGACCT, GATACCT, TACCACT, GAGACCT} by sorting the elements of S into reverse lexicographic order $B_{SAP}(n)$. This permutes the symbols within SAP-intervals to minimize the number of runs.

Figure 5:
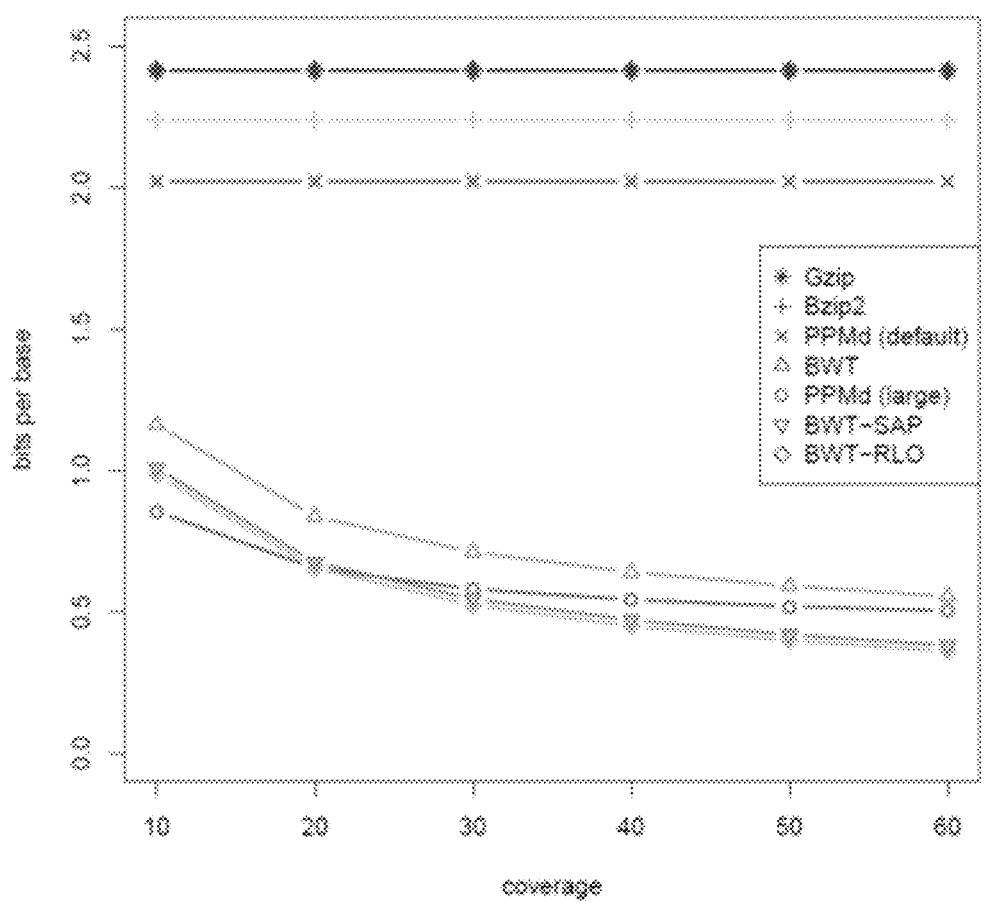

FIG. 5 demonstrates a comparison of different compression strategies on a simulated sequence run. The x axis is sequencing depth coverage whereas the y axis is number of bits used per input symbol. Gzip, Bzip2, PPMd (default) and PPMd (large) demonstrate compression achieved on the raw sequence data. BWT, BWT-SAP and BWT-RLO demonstrate first stage compression results on the BWT using PPMd (default) as second-stage compressor.

DEFINITIONS

As used herein, the term "Burrows Wheeler transform" or "BWT" refers to a data structure used to permute, or rearrange, a data string or text. The BWT reorders characters in an original data string or text such that like characters tend to be grouped together. The grouping of like characters makes them easier to compress. The BWT does not itself compress a data set or text, but instead transforms it into a file that is more favorable to compression. A BWT-permuted file can be compressed by standard techniques for data compression algorithms based on the BWT. For example, a file transformed by means of the BWT can be further processed by Move-to-front encoding and then Huffman encoding algorithms that result in the compression of the dataset or text. Such methods will typically compress the BWT-permuted text into a smaller size than would be achieved if the same techniques were to be applied to the original, untransformed text. At the same time, the BWT also retains the ability to reconstruct the original text in such a way that the original input information is not lost. The transform is accomplished by sorting, in lexicographic order, a data string into all possible rotations and extracting the last character from each rotation, resulting in a string of characters that is more favorable to compression.

As used herein, the term "data strings" refers to a group or list of characters derived from a data set. As used herein, the term "collection," when used in reference to "data strings" refers to one or more data strings. A collection can comprise one or more data strings, each data string comprising characters derived from a data set. A collection of data strings can be made up of a group or list of characters from more than one data set, such that a collection of data strings can be, for example, a collection of data strings from two or more different data sets. Or, a collection of data strings can be derived from one data set. As such, a "collection of characters" is one or more letters, symbols, words, phrases, sentences, or data related identifiers collated together, wherein said collation creates a data string or a string of characters. Further, a "plurality of data strings" refers to two or more data strings. In one embodiment, a data string can form a row of characters and two or more rows of characters can be aligned to form multiple columns. For example, a collection of 10 strings, each string having 20 characters, can be aligned to form 10 rows and 20 columns.

As used herein, the term "augmenting the Burrows Wheeler transform" refers to increasing the Burrows Wheeler transform. For example, augmenting a BWT comprises the merging of characters of a collection of data strings in a character by character manner, wherein the BWT increases in the number of merged characters with each subsequent insertion of new characters, as such the BWT increases with each character insertion.

As used herein, "incrementally building a Burrow Wheeler transform" refers to increasing the BWT in a step by step manner. For example, characters from a collection of data strings can be added character by character to the computer implemented methods described herein, as such the BWT is updated or built following each subsequent insertion of characters. As such, the BWT is changed or updated after each incremental addition of characters.

As used herein, the term "concatenate strings" and permutations thereof refers to the joining of strings, for example strings of data or data strings, end to end. For example, a concatenation of two words w and v, written wv, is the string comprising the symbols of w followed by the symbols of v.

As used herein, a "subsequence", "substring", "prefix" or "suffix" of a string represents a subset of characters, letters, words, etc, of a longer list of characters, letters, words, etc., (i.e., the longer list being the sequence or string) wherein the order of the elements is preserved. A "prefix" typically refers to a subset of characters, letters, numbers, etc. found at the beginning of a sequence or string, whereas a "suffix" typically refers to a subset of characters, letters, numbers, etc. found at the end of a string. Substrings are also known as subwords or factors of a sequence or string.

As used herein, the terms "compression boosting strategy" or "compression boosting method" refers to the reordering of data prior to or concurrent with building the BWT (e.g., in addition to sorting carried out during normal BWT build processes). Compression boosting results in the resorting of data that is not practiced by the Burrows Wheeler Transform that results in a BWT that is more compressible by standard text compression methods (e.g., second stage compression methods) than would be the case if these methods were not employed. The strategies disclosed herein modify the BWT algorithms to resort the input data resulting in BWT output of a resorted set of data that is more compressible than the BWT of the original collection. The reverse lexicographic ordering (RLO) and same-as-previous (SAP) methods described herein are compression boosting methods.

DETAILED DESCRIPTION

The present disclosure describes methods and systems for computing the Burrows Wheeler transform of a collection of data strings by building or augmenting the BWT in a character by character cumulative manner along a collection of data strings. In some embodiments the BWT is augmented or built in a character-by-character, cumulative manner. By computing the BWT using methods set forth herein it is not necessary to create a suffix array or concatenate the data strings prior to computing the transform. The methods and systems can be used on any length data strings from a variety of data sources, such as those generated during sequencing (e.g. nucleic acids, amino acids), language texts (e.g. words, phrases, and sentences), image derived (e.g. pixel map data), and the like. The datasets can be datasets as found on, for example, a computer storage medium, or datasets can be those generated live or in real time, such as while an event or assay is in progress. The methods and systems described herein can further accommodate the addition and/or removal of one or more data strings in a dynamic fashion. The new computational methods and systems disclosed herein allow for increases in time efficiency and computer space usage which complements and provides for further advancement in technological areas where large data sets are the norm. Such technologies, for example sequencing technologies, would greatly benefit with more advanced computational methods not only to deal with current computational challenges, but also provide space for further technological advances in their own fields.

The outcome of a sequencing experiment typically comprises a large number of short sequences, often called "reads", plus metadata associated with each read and a quality score that estimates the confidence of each base in a read. When compressing the DNA sequences with standard text compression methods such as Huffman and Lempel-Ziv, it is hard to improve substantially upon the naïve method of using a different 2-bit code for each of the 4 nucleotide bases. For example, GenCompress (Chen et al, 2002, Bioinformatics 18:1696-1698, incorporated herein by reference in its entirety) obtains 1.92 bits per base (bpb) compression on the E. coli genome, only 4% below the size taken up by 2-bits-per-base encoding An investigator desiring to sequence a diploid genome (e.g., a human genome) might desire 20 fold average coverage or more with the intention of ensuring a high probability of capturing both alleles of any heterozygous variation. This oversampling creates an opportunity for compression that is additional to any redundancy inherent in the sample being sequenced. However, in a whole genome sequencing experiment, the multiple copies of each locus are randomly dispersed among the many millions of reads in the dataset, making this redundancy inaccessible to any compression method that relies on comparison with a small buffer or recently seen data. One way to address this redundancy is through "reference based" compression (Kozanitis et al., 2010, In RECOMB, Vol. 6044 of LNCS, p. 310-324. Springer; Fritz et al., 2011, Gen Res 21:734-740, both of which are incorporated herein in their entireties) which saves space by sorting aligned reads based on their positional alignment to a reference sequence, and expressing their sequences as compact encodings of the differences between the reads and the reference. However, this is fundamentally a lossy strategy that achieves best compression by retaining only reads that closely match the reference (i.e., with few or no differences). Retaining only those reads that might closely match a reference would limit the scope for future reanalysis of the sequence, such as realignment to a refined reference sequence which might have otherwise have uncovered. For example, specific haplotypes (e.g., associated with disease or therapeutic efficacy disposition of a subject) or any other sort of de novo discovery on reads that did not initially align well would be missed by employing such a referenced based computational strategy. Moreover, a reference based approach is inapplicable to experiments for which a reference sequence is not clearly defined, for example for metagenomics, or for experiments wherein there is no reference sequence, for example for de novo sequencing.

A lossless compression method for sets of reads, ReCoil (Yanovsky, 2011, Alg for Mol Biol 6:23, incorporated herein by reference in its entirety) employs sets of reads that works in external memory (e.g. with sequence data held on external storage devices such as disks, etc.) and is therefore not constrained in scale by available RAM. A graph of similarities between the reads is first constructed and each read is expressed as a traversal on that graph, encodings of these traversals then being passed to a general purpose compressor (ReCoil uses 7-Zip). The two-stage nature of this procedure is shared by the family of compression algorithms based on the BWT. The BWT is a permutation of the letters of the text and so is not a compression method per se. Its usefulness for compression is derived from the provisions that the BWT tends to be more compressible than its originating text; it tends to group symbols into "runs" of like letters which are easy to compress, and further is able to reconstruct the original text without loss of information. Thus the BWT itself can be viewed as a compression-boosting technique in the sense we use this term herein. Once generated, the BWT is compressed by standard techniques; a typical scheme would follow an initial move-to-front encoding with run length encoding followed by Huffman encoding.

The widely used BWT based compressor, bzip2, divides a text into blocks of at most (and by default) 900 kbytes and compresses each separately such that it is only able to take advantage of local similarities in the data. Mantaci et al (2005, In CPM 2005 Vol. 3537 of LNCS, p. 178-179, incorporated herein by reference in its entirety) provided the first extension of the BWT to a collection of sequences and used it as a preprocessing step for the simultaneous compression of the sequences of the collection. Mantaci et at showed that this method was more effective than the technique used by a classic BWT based compressor because one could potentially access redundancy arising from the long range correlations in the data. Until recently computing the BWT of a large collection of sequences was prevented from being feasible on very large scales by the need to either store the suffix array of the set of reads in RAM or to resort to "divide and conquer then merge" strategies at considerable cost in CPU time. BWT is further explained, for example, in Adjeroh et al. (2008, The Burrows Wheeler Transform: Data Compression, Suffix Arrays and Pattern Matching, Springer Publishing Company; incorporated by reference herein in its entirety).

Several methods are disclosed herein for computing the BWT of large collections, such as DNA sequences, by making use of sequential reading and writing of files from a disk. For example, algorithm1 only uses approximately 14 bytes of RAM for each sequence in the collection to be processed and is therefore capable of processing over 1 billion reads in 16 bytes of RAM, whereas the second variant algorithm2 uses negligible RAM at the expense of a larger amount of disk I/O.

Described herein are algorithms that are fast, RAM efficient methods capable of computing the BWT of sequence collections of the size encountered in human whole genome sequencing experiment, computing the BWT of collections as large as 1 billion 100-mers. Unlike the transformation in Mantaci et al. the algorithms disclosed herein comprise ordered and distinct "end-marker" characters appended to the sequences in the collection, making the collection of sequences an ordered multiset, for example the order of the sequences in the collection is determined by the lexicographical order of the end-markers. Ordering of sequences in the collection can affect the compression since the same or similar sequences might be distant in the collection.

Three algorithmic variations (e.g. algorithm1, algorithm2 and algorithm3) are described herein, all of which compute the Burrows Wheeler transform in a similar fashion, building the BWT character by character, along a collection of data strings. Computing the BWT on data sets in a step by step fashion, building the BWT cumulatively along the data strings, provides many benefits including, but not limited to, the ability to access the intermediate BWT files for performing additional operations (for example locating and/or counting patterns in data strings, etc.), time efficiencies in computing the final BWT of a collection of strings, storage efficiencies in utilizing less computer storage, and usage efficiencies in that utilization of the algorithms described herein utilize minimal to no RAM for working the BWT.

To demonstrate the manner in which the algorithms compute the BWT of a dataset, assume that an exemplary collection of data strings is derived from a collection of sequence data, the exemplary strings being 100-mers. In this example there are therefore 100 characters of data (i.e., one nucleotide designator for example A, C, G, T, U or N (undefined)) in a data string. Also assume, for this example, that there are 10 data strings in the collection. Working in a character-by-character fashion along a string of data, the algorithms compute the BWT for a collection consisting of a first character in each string (i.e., a collection of 10 characters, one from each string). A second collection of characters, consisting of the next character in each string adjacent to the first character in each string, is merged with the collection of first characters and the BWT is augmented, or incrementally built, by cumulatively merging the collection of second characters with the collection of first characters. The process is continued for the collection of third characters adjacent to the respective second characters of each string and the collection of third characters is merged with the two previous collections of characters such that the BWT is again augmented to include cumulatively the first, second and third characters from each string. The process can be iteratively repeated until the whole of the characters 100 to 1 (reading right to left through the string) have been merged and a final BWT computed for all of the characters in the collection of ten 100-mer data strings. In this way, the algorithms build the BWT by successively inserting characters from a data string into previously merged characters, preferably in a right to left manner, augmenting or incrementally building the BWT after each merge, until all characters in a data string have been added and a final BWT is computed on the complete data string. Depending upon the nature of the data and/or its use, the data can read in a left to right direction and used to augment the BWT.

The methods and systems described herein are not limited to the size of the data strings. The aforementioned example exemplifies the use of the disclosed algorithms with reference to 100-mers, however data strings of any length can be used with methods and systems described herein. Further, the aforementioned example describes the use of the disclosed algorithms with reference to a data set derived from a nucleic acid sequence, however datasets from any source, biological or non-biological, can be used with methods and systems described herein. Examples of dataset sources include, but are not limited to, nucleic acid sequences (as exemplified above), amino acid sequences, language text data sets (i.e., sequences of words, sentences, phrases, etc.), image derived datasets and the like. Further, a plurality of datasets is envisioned for use with methods and systems as described herein. Furthermore, although the data strings in the above example were all of the same length (100 characters), the data strings need not be of uniform length. Rather data strings having varying lengths can be used in a method set forth herein.

The algorithms described herein compute the BWT on a collection of data strings from a data set in the same manner;

however each variation provides alternatives in dealing with the data strings. For example, the first variant, algorithm1, is favorable for computing the BWT on live generated data, for example data that is being produced as the BWT is being augmented. Algorithm1 is typically faster at computing the BWT than algorithm2 or algorithm3; however it also typically utilizes more memory for implementation than algorithm2 or algorithm3. The second variant, algorithm2, may be considered favorable for computing the BWT on data that is stored in external folders such as those maintained on a computer readable storage medium like a hard drive, etc. The third variant, algorithm3, provides a modification to algorithm2 wherein the modification can allow for even greater efficiencies in computer storage and usage by accessing a portion of the whole data string, the prefix of a data string, such that it is not necessary to access the whole data string every time for building the BWT in a character by character fashion. As such, a user has options for deciding which algorithm to utilize depending on, for example, a user defined need for speed over computer memory usage, and vice versa. Even though algorithms1, 2 and 3 as described offer alternatives for data compression, it is contemplated that they are not limited to those particular modifications. For example, the ability of accessing the prefix of a data string could be written into algorithm1, or real time data access could be written into agorithm3, etc. As such, the algorithms described herein offer different alternatives which a skilled artisan could utilize depending on need.

Certain illustrative embodiments of the invention are described below. The present invention is not limited to these embodiments.

Embodiments as disclosed herein provide solutions to problems associated with data compression and in particular to computing the Burrows-Wheeler transform (BWT) of datasets, for example large data sets. The disclosed embodiments present algorithms capable of computing the BWT of very large string collections. The algorithms are lightweight in that the first algorithm, algorithm1, uses O(m log mk) bits of memory to process m strings and the memory requirements of the second algorithm, algorithm2, are constant with respect to m. As such, algorithm1 and algorithm2 offer advantages from prior BWT utilization such that their computation does not require string concatenation or the need to create a suffix array prior to performing the BWT on a dataset. The algorithms as described herein were evaluated, for example as presented in Example 2, on data collections of up to 1 billion strings and their performance compared to other approaches on smaller datasets. Although tests performed were on collections of DNA sequences of uniform length, the algorithms are not limited by the length of a data string and apply to any string collection over any character or language alphabet. The computational methods utilizing the algorithms described herein use minimal or no RAM which allows for computations to be performed on computers of any size and memory capacity. Further, with regards to applying the disclosed algorithms for genomic sequencing, the disclosed computational methods provides for real-time or on the fly sequencing, such as building the BWT of a data set as the sequencing assay is being performed, cycle by cycle. Thus the BWT can be augmented with a first subset of characters from a collection of sequence strings prior to the complete acquisition of the characters in the sequence string. In other words, a second subset of characters in the collection of sequence strings can be acquired after the BWT is augmented with the characters from the first subset of characters.

For example, computational methods utilizing the disclosed algorithms allow for the BWT to be built after each individual sequencing cycle (e.g., of a sequence by synthesis reaction, sequence by ligation cycle reaction, etc.) the result of which can be merged/inserted to the previous cycle. As sequencing progresses a user can perform the BWT at any point during a sequencing assay as it occurs, not only when all the data is compiled at the end of a sequencing assay. For example, a computer implemented method for performing the BWT during a sequencing assay could interrogate the BWT index at the completion of one or more sequencing cycles, optionally reporting the matches identified on a display device (i.e., monitor, screen, etc.). Such an interrogation or query could be, for example, programmed by a user to occur at a given cycle, or the query could be triggered by a user at any given time. The results could be output in a number of different ways, for example, results could be reported on a computer monitor or screen and the results could be accessed remotely via an Internet connection by, for example, triggering the query via a web browser which reports results via a web page.

Of course, the algorithms as described herein can be used at the end of each sequencing run, however it is contemplated that the real time sequencing aspect provided by utilizing the computational methods incorporating the algorithms as described herein provides a user with the ability to build the BWT for a sequence on a cycle by cycle basis which has not been previously available. Such sequencing offers myriad advantages to an investigator including, but not limited to, aborting a sequencing run thereby saving reagents and time if a sequencing run appears suboptimal, ability to accessing sequencing data for additional operations prior to the completion of a sequencing assay, determining sequences associated with disease faster for rapid diagnosis (e.g. before the entire genome sequence of a diagnostic sample has been fully acquired), stopping a run when the sequence of interest is determined thereby saving time and reagents, etc.

Embodiments of the present disclosure provide utility in the biological arts. For example, computational methods utilizing the algorithms disclosed herein are applicable to the fields of genomic DNA and RNA sequencing, resequencing, gene expression analysis, drug discovery, disease discovery and diagnosis, therapeutics and disease related treatment response, prognostics, disease correlations, evolutionary genetics, etc. The methods can be particularly useful for example applications wherein experimental results oftentimes produce large datasets.

However, the algorithms as described herein are not limited to the field of genomic sequencing, but also find utility for any of a variety of large data sets for general signal processing, text indexing, information retrieval and data compression fields.

The present disclosure provides novel algorithms and computer implemented methods and systems of their use for constructing the BWT in external memory. These algorithms and their computer implemented methods and systems of use are particularly applicable to DNA data, however they are not limited to DNA data and find utility in other applications where large data sets exist such as language texts, image derived data sets, and the like. In embodiments herein, the novel algorithms and their computer implemented methods and systems of use can be applied to any size of dataset, however particular utility is realized when the BWT is to be generated from a dataset comprising a large collection of data strings for example datasets of at least 25 million characters, at least 50 million characters, at least 100 million characters, at least 500 million characters, at least 750 million characters, at least 1 billion characters, at least 10 billion characters, at least 50 billion characters, at least 100 billion characters, at least 1 trillion or terabase characters, at least 10 trillion characters, at least 50 trillion characters, or at least 100 trillion characters.

The present disclosure provides methods and systems for determining the Burrows Wheeler transform of a collection of strings, for example strings derived from large datasets, further without the need to determine the suffix array from the strings and without the need to concatenate the strings. The BWT determined by practicing the methods and systems as described herein is compressible and storable in external files such that little or no computer RAM is utilized. Further, methods and systems are described herein that comprise compression-boosting strategies, producing a BWT that is more compressible by standard text compression methods (e.g., second stage compression methods) than would be the case if these strategies were not employed. Such strategies include embodiments for sorting or reordering the members of a collection of strings such that the BWT of the reordered collection is more compressible by standard text compression strategies than is the BWT of the collection in its original order. The strategies disclosed herein provide methods for computing a compression-boosting reordering of the sequences in the collection while the BWT of the collection is being constructed, such that the algorithm directly outputs the BWT of a permuted collection that is more compressible than the BWT of the original collection.

For a collection of m strings of length k, the algorithms are lightweight in that an individual uses only $O(m \log(mk))$ bits of space and $O(k \text{ sort}(m))$ time (algorithm1), where sort (m) is the time taken to sort m integers and computations are performed almost entirely in external memory, taking $O(km)$ time (algorithm2) with RAM usage that is constant for collections of any size, dependent only on the alphabet size and therefore negligible for DNA data. The overall I/O (input/output) volume is $O(k^2 m)$. The algorithms as described herein are scan-based in the sense that all files are accessed in a manner that is entirely sequential and either wholly read-only or wholly write-only.

Experiments were performed to compare the algorithms as described herein to those of Siren (2009, In: SPIRE vol. 5721 of LNCS, pp. 63-74, Springer; incorporated herein in its entirety) and Ferragina et al. (2010, In: LATIN vol. 6034 of LNCS, pp. 697-710, Springer; incorporated herein by reference in its entirety). Further, computational experiments were performed to assess the performance of the algorithms as described herein to string collections as large as one billion 100 mers.

As preliminaries, let $\Sigma=\{c_1, c_2, \ldots, c_\sigma\}$ be a finite ordered alphabet with $c_1 < c_2 < c_\sigma$, where < denotes the standard lexicographic order. Given a finite string $w=w_0 w_1 \ldots w_{k-1}$ each $w_i \in \sigma$, a substring of a string w is written as $w[i,j]=w_i \ldots w_j$. A substring of type w [0, j] is called a prefix, while a substring of type w [i, k-1] is called a suffix. As described herein, the j-suffix is the suffix of w that has length j. The concatenation of two words w and v, written wv, is the string comprising the symbols of w followed by the symbols of v.

Let $S=\{S_1, S_2, \ldots, S_m\}$ be a collection of m strings, each comprising k symbols drawn from $\Sigma$. Each $S_i$ can be imagined to have appended to it an end marker symbol $ that satisfies $<c_1$. The lexicographic order among the strings is defined in the usual way, such as found, for example in Flicek and Birney (2009, Nat Meth 6:6S-S12) and Bioinformatics; Sequence and Genome Analysis, 2004, 2$^{nd}$ Ed., David Mount, Cold Spring Harbor Laboratory Press, both of which are incorporated herein by reference in their entireties, except that each end marker $ is considered a different symbol such that every suffix of every string is unique in the collection. The end marker is in position k, i.e. $S_i[k]=S_j[k]=\$$, and $S_i[k]<S_j[k]$ is defined, if i<j. The 0-suffix is defined as the suffix that contains only the end marker $.

The suffix array SA of a string w is the permutation of integers giving the starting positions of the suffixes of w in lexicographical order. The BWT of w is a permutation of its symbols such that the i-th element of the BWT is the symbol preceding the first symbol of the suffix starting at position SA[i] in w, for i=0, 1, ..., k (assuming the symbol preceding the suffix starting at the position 0 is $). A skilled artisan will understand suffix arrays and the Burrows-Wheeler transform, however further reading can be found at, for example, Puglisi et al. (2007, ACM Comput Sury 39), Adjeroh et al. (2008, The Burrows-Wheeler Transform: Data Compression, Suffix Arrays and Pattern Matching, Springer, 1$^{st}$ Ed.) and Li and Durbin (2009, Bioinformatics 25:1754-1760), all of which are incorporated herein by reference in their entireties.

Described herein are algorithms for use in computer implemented methods that compute the BWT of a collection of strings without concatenating the strings and without the need to compute their suffix array. These algorithms are particularly applicable to methods and systems for use in defining large data sets. With regards to the algorithms, it is assumed that j=1, 2, ..., k and i=1, 2, ..., m. The algorithms compute the BWT of a collection S incrementally via k iterations. At each of the iterations j=1, 2, ..., k−1, the algorithms compute a partial BWT string $bwt_j(S)$ by inserting the symbols preceding the j-suffixes of S at their correct positions into $bwt_{j-1}$ (S). Each iteration j simulates the insertion of the j-suffixes in the SA. The string $bwt_j$ (S) is a "partial BWT" in that the addition of m end markers in their correct positions would make it the BWT of the collection $\{S_1 [k-j1, k], S_2 [k-j-1, k], \ldots, S_m[k-j-1, k]\}$.

A trivial "iteration 0" sets the initial value of the partial BWT by simulating the insertion of the end markers $ in the SA. Since their ordering is determined by the position in S of the string they belong to, $bwt_0$ (S) is just the concatenation of the last non-$ symbol of each string, that is $S_1 [k-1] S_2 [k-1] \ldots S_m [k-1]$.

Finally, iteration k inserts m end markers into $bwt_{k-1}$ (S) at their correct positions. This simulates the insertion of the suffixes corresponding to the entire strings into the SA.

As in Ferragina et al., the observation is such that going from $bwt_{j-1}$ (S) to $bwt_j$ (S) at iteration j required only that one insert m new symbols and does not affect the relative order of the symbols already in $bwt_{j-1}$ (S). The equation $bwt_j$ (S) can be thought of as being partitioned into $\sigma+1$ strings $B_j$ (0), $B_j$ (1), ..., $B_j$ ($\sigma$), with the symbols in $B_j$ (h) being those that are associated with the suffixes of S that are of length j or less and begin with $c_0=\$$ and $c_h \in \Sigma$, for h=1, ..., $\sigma$. It is noted that $B_j$ (0) is constant for all j and, at each iteration j, $B_j$ (h) is stored in $\sigma+1$ external files that are sequentially read one by one.

During the iteration j=1, ..., k, the symbol associated with the new suffix $S_i$ [k−j, k] of each string $S_i \in S$ (this symbol is $S_i$ [k−j−1] for j, k, or $ at the final iteration) is inserted into the BWT segment $B_j(z)$, where $c_z=S_i$ [k−j] $B_j(z)$ contains all symbols associated with suffixes starting with the symbol $c_z$. It was contemplated that the position in $B_j(z)$ where this symbol needs to be inserted can be computed from the position r where, in the previous step, the symbol $c_z$ has been inserted into the BWT segment $B_{j-1}(v)$, where $c_v=S_i$ [k−(j−1)], recalling that $B_{j-1}(v)$ contains all symbols associated with suffixes that have already been inserted and that start with the symbol $c_v$.

To facilitate the computation, one retains the BWT segments $B_{j-1}$ (h), for $0 \leq h \leq \sigma$, and tracks the positions within the segments of the symbols that correspond to the (j−1) suffixes of S, which is accomplished by associating to each $B_{j-1}(h)$ an array $P_{j-1}(h)$ of integers that stores the absolute positions of the (j−1) suffixes starting with $c_h$. Each $P_{j-1}(h)$ is in turn associated with an array $N_{j-1}(h)$ that has the same number of entries and is such that $N_{j-1}(h)[q]$ stores i, the original position in S of the string $S_i$ whose (j−1) suffix is pointed to by $P_{j-1}(h)[q]$. Here q is a generic subscript of the array $N_{j-1}(h)$ or $P_{j-1}(h)$. The maximum value of q is determined by the number of (j−1) suffixes starting with $c_h$ and will therefore vary with both h and j.

At the start of iteration j, it is assumed that the following structures are available for each h=0, ... σ, where $c_0$=$ and $c_n \in \Sigma$, for n=1, ..., σ and the maximum value of q depends on the number of the (j−1) suffixes starting with $c_h$:

$B_{j-1}(h)$ is a segment of the partial BWT;

$N_{j-1}(h)$ is an array of integers such that $N_{j-1}(h)[q]$ is associated with the (j−1) suffix of the string $S_i \in S$, where $i=N_{j-1}(h)[q]$;

$P_{j-1}(h)$ is an array of integers such that $P_{j-1}(h)[q]$ is the absolute position of the symbol $S_i[k-j]$, associated with the (j−1) suffix of $S_i$, in $B_{j-1}(h)$, where $i=N_{j-1}(h)[q]$.

Hence, at the end of the iteration j−1, for each element in $N_{j-1}$ and $P_{j-1}$, the symbol $c_z=S_i[k-j]$, with $i=N_{j-1}(v)[q]$, has been inserted in the position $P_{j-1}(v)[q]$ in $B_{j-1}(v)$, where $c_v=S_i[k-(j-1)]$.

During the iteration j, the structures are updated for each string $S_i \in S$. The point is to insert the new symbol associated with the j-suffix of $S_i$ into $B_{j-1}(z)$, where $c_z=S_i[k-j]$, for some z=1, ..., σ, at its correct position in order to obtain $B_j(z)$. Hence, the task is to compute $P_j(h)$ by considering how many suffixes of S that are at length j or less are smaller than each suffix of length j.

The following lemma is directed to this point and is based on a function called LF-mapping (Ferragina and Manzini, 2005, J ACM 52:552-581) that is also used in compressed self-indexes. The method is based on the count of symbols, from first position to the position of the last inserted symbol of $S_i$ in $bwt_{j-1}(S)$, that are smaller than $c_z=S_i[k-j]$. It is equivalent to counting the number of symbols that are associated with suffixes smaller than $S_i[k-j, k]$. However, it is not required to do exactly this, because the suffixes starting with a symbol smaller than $c_z$ are associated with symbols in $B_{j-1}(r)$ for r=0, ..., z−1. So, all that is needed is to count how many suffixes of length j or less starting with the symbol $c_z$ are smaller than the suffix $S_i[k-j, k]$.

Lemma 1.

For any iteration j=1, 2, ..., k, given a symbol $c_h$, with 0≤h≤σ, let q be an index that depends on the number of the (j−1)-suffixes starting with $c_h$. For each string $S_i \in S$, with $i=N_{j-1}(h)[q]$, it is assumed that the suffix $S_i[k-(j-1), k]$ is lexicographically larger than $r=P_{j-1}(v)[q]$ suffixes of length 0, 1, ..., j−1 that begin with the symbol $c_v=S_i[k-(j-1)]$. Now, $c_z=S_i[k-j]$ is fixed. Then, the new suffix $S_i[k-j, k]$ $c_z S_i[k-(j-1), k]$ is lexicographically larger than r' suffixes of length 0, 1, ..., j, where r'=rank($c_z$, r, $c_v$) and rank($c_z$, r, $c_v$) denotes the number of occurrences of $c_z$ in $B_{j-1}(0) ... B_{j-1}(v-1)B_{j-1}(v)[0, r-1]$.

Proof By hypothesis $c_z=S_i[k-j]$ and $c_v=S_i[k-(j-1)]$. Clearly, $S_i[k-j, k]$ is larger than the suffixes starting with a symbol smaller than $c_z$ (they are associated with the symbols in $S_{j-1}(0), ... B_{j-1(z-1)}$)), and is smaller than all suffixes starting with a symbol greater than $c_z$ (they are associated with the symbols in $B_{j-1}(z+1), ..., B_{j-1}(\sigma)$. Since the suffixes starting with $c_z$ are associated with the symbols in $B_{j-1}(z)$, the correct position of the symbol associated with the suffix $B_i[(k-j,k]$ is in $B_{j-1}(z)$. Computation of how many suffixes of length j or less starting with $c_z$ are smaller than $B_i[k-j,k]$ is performed. The sorting of the rows in BWT implies that counting how many suffixes starting with $c_z$ in $\{S_1[k-j,k], S_2[k-j,k], ... S_m[k-j,k]\}$ that are smaller than $S_1[k-j,k]$ is equivalent to counting the number of occurrences of $c_z$ in $B_{j-1}(0), ..., B_{j-1}(v-1)$ and in $B_{j-1}(v)[0, r-1]$. This is rank($c_z$, r, $c_v$).

The position of each j-suffix $S_i[k-j,k]$ are computed using Lemma 1 and stored in $P_j$ according to the symbol $S_i[k-j]$. In other words, if $c_z=S_i[k-j]$, the computed position r' corresponds to the absolute position in $S_j(z)$ where is inserted the new symbol associated with $S_1[k-j,k]$ starting with $c_z$. This means that, for each symbol $c_h$, with 0≤h≤σ, it is considered, in the computation of the new positions, all new j-suffixes in S that being with $c_h$. Hence, if $S_r[k-j]=S_z[k-j]$ and $S_r[k-(j-1), k]<S_s[k-(j-1),k]$, for some 1≤r, s≤m, it follows that $S_r[k-j, k]<S_s[k-j,k]$. For this reason and since each $B_j(h)$ is stored in an external file, each $B_j(h)$ respectively $N_j(h)$ is sorted and insert the new symbols according to the value of their position, from the smallest to the largest. Given this information, one can build $B_j(h), ..., B_j(\sigma)$ by using the current filed $B_{j-1}(1), ..., B_{j-1}(\sigma)$. Each external file associated with each $B_j(h)$ is read once, in a sequential fashion, and insert all symbols associated with the j-suffixes starting with the symbol $c_h$. Once all the symbols are read and copied, $B_{j-1}(0), ..., B_{j-1}(\sigma)$ respectively, i.e. the partial BWT string required by the next iteration. Since $P_{j-1}(h)$ and $B_{j-1}(h)$ is no longer needed, one can write $P_j(h)$ and $B_j(h)$ over the already processed $P_{j-1}(h)$ and $B_{j-1}(h)$.

The counts for $B_{j-1}(d)$, $c_d<S[k-j]$ are dealt with by keeping a count of the number of occurrences of each symbol for all $B_{j-1}(h)$ in memory, which takes $O(\sigma^2 \log(mk))$ bits of space. For $B_{j-1}(z)$, $c_z=S[k-j]$, the pointer value corresponding to S- which is read from $P_{j-1}(h)$ which shows how far along the count needs to proceed in $B_{j-1}(z)$. So for each $B_{j-1}$. $O(\sigma^2 \log(mk))$ bits of space are needed; a trivial amount for DNA data.

The steps at the iteration j can be described in the following way:

1. For each symbol $c_v$, with 0≤v≤σ and for each element q (it is observed that the maximum value of q depends on the number of the (j−1)-suffices starting with $c_v$), it is known:

The number of the sequence $i=N_{j-1}(v)[q]$ (clearly $S_i[k-(j-1)]=c_v$).

$r=P_{j-1}(v)[q]$ (it means that $c_z=S_i[k-j]$ has been inserted in the position r of $B_{j-1}(v)$ at the end of the previous step).

By using $c_z$, r and $c_v$, r'=rank($c_z$, r, $c_v$) is computed (see Lemma 1), i.e. the position at which the new symbol in $B_j(z)$ is to be inserted. r is stored into $P_j(z)$.

i is stored into $N_j(z)$.

It was observed that there was no need to store $c_z$, because the symbol $c_z$ can be read from $B_{j-1}(v)$ when the new position is computed.

2. For each symbol, $c_z$, with 0≤z≤σ, the pair ($P_j(z)$, $N_j(z)$) is sorted in ascending order, where $P_j(z)$ is the primary key.

3. For each symbol $c_z$, with 0≤z≤σ, and for each element q (where the maximum value of q depends on the number of the j-suffixes starting with $c_z$), the new symbol associated with j-suffix of the string $S_i$ is inserted, where $i=N_j(z)[q]$, into $B_j(z)$ in the position $P_j(z)[q]$.

4. Return $B_j$, $P_j$, $N_j$.

The two new algorithms, herein called algorithm 1 and algorithm2, can now be compiled. Both are based on the above description, but differ in the data structures used. Algorithm 1 uses more internal memory and takes less time, whereas for small alphabets, such as an alphabet comprising the four canonical bases of a sequence, or ACGT, the second algorithm uses minimal or no memory at all.

Algorithm1

In the above description, $P_j(h)$ and $N_j(h)$ is used for each symbol $c_h$, with $0 \leq h \leq \sigma$, whereas in the implementation of the first algorithm, for each iteration j, a unique array $P_j$ for all $P_j(h)$ and a unique array $N_j$ for all $N_j(h)$ in internal memory is allocated. It was observed that $P_j$ and $N_j$ contains exactly one integer for each sequence in the collection, $P_j$ uses O(m log (mk)) bits of workspace and $N_j$ uses O(m log m) bits of workspace. Since $P_j[q]$, for some q, denotes the position into $B_j(z)$ of the new symbol associated with the j-suffix $S_i[k-j, k]$ starting with $c_z = S_i[k-j]$ and $i = N_j[q]$, another array $Q_j$, setting $Q_j[q]$=is used. It uses O(m log σ) bits of workspace. It is not desired to read the a external files containing the BWT segments $B_j$, more than once and since the values in $P_j$ are absolute positions (as previously described), the values in $P_j$ are to be sorted before inserting the new symbols. The first, second and third keys of the sort are the values in $Q_j$, $P_j$, and $N_j$ respectively. It is not necessary to store the associated suffixes in memory, so this algorithm uses O(m log(mk)) bits of workspace and O(k sort(m)) of time, where sort(m) is the time needed to sort $Q_j$, $P_j$, and $N_j$. It is observed that if $Q_j$, $P_j$, $N_j$ are stored in external files and use an external sorting algorithm, the workspace can be significantly reduced.

Algorithm2

The second algorithm is based on least-significant-digit radix sort (see Corman et al., 1991, Introduction to Algorithms, $5^{th}$ Ed., McGraw Hill, incorporated herein by reference in its entirety). For this variant, sorting of arrays is not required because the sequences themselves are sorted externally. At the start of iteration j, the elements of S are assumed to be ordered by (j−1)-suffix, this ordering being partitioned into external files $T_{j-1}(1), \ldots T_{j-1}(\sigma)$ according to the first characters of the (j−1)-suffices. Files $P_{j-1}(1), \ldots, P_{j-1}(\sigma)$ are such that $P_{j-1}(h)$ contains the positions of the (j−1)-suffixes in $B_{j-1}(h)$, ordered the same way.

All files are assumed to be accessed sequentially via read-only R( ) or write-only W( ) file streams. In the order $h=1, \ldots \sigma$, read-only file streams are opened to each of $T_{j-1}(h)$ and $P_{j-1}(h)$, while two read-only file streams $R_1 (B_{j-1}(h))$ and $R_2 (B_{j-1}(h))$ reading from each segment of the partial BWT remain open throughout the iteration.

An observation is that since the strings of S are presented in (j−1)-suffix order, so also is the subset whose (j−1)-suffixes share a common first symbol $c_h$. Thus it is $R_1 (B_{j-1}(h))$ to count the number of occurrences of each symbol seen so far in $B_{j-1}(h)$, keeping track of how far into $B_{j-1}(h)$ one has read so far. One then reads forward to the position pointed to by P, updating the counts along the way. Since the strings are processed in (j−1)-suffix order, backtracking is not needed.

Having determined where to put the new BWT symbol $S[k-j-1]$ in $B_{j-1}(z)$, where $c_z + S[k-j]$, $R_2 (B_{j-1}(z))$ is used to read up to that position, then write those symbols plus the appended $S[k-j-1]$ to $W(B_j(z))$. All strings S' whose symbols need to be inserted into $B_{j-1}(z)$ arrive in (j−1)-suffix order and also satisfy $S'[k-j]=c_z$. They are therefore j-suffix ordered so; again, backtracking is not needed.

Finally, to $W(P_j(z))$ is written the entry that corresponds to S. To do this, one tracks the number of additional symbols that have so far been inserted between the symbols from $B_{j-1}(z)$ and sent to $W(B_j(z))$. This provides an offset that is added to the number of symbols read from $R_2 (B_{j-1}(h))$ so far to create the needed value.

Once the last element of $T_{j-1}(\sigma)$ has been read, the cumulative count values are updated to reflect any symbols not yet read from each $R_1 (B_{j-1}(h))$ and send any symbols not yet read from $R_2 (B_{j-1}(h))$ to $W(B_j(h))$. FIG. 3 uses a simple example to illustrate how the data structures associated with both variants of the algorithm are updated during an iteration.

to Algorithm2 utilizes minimal to virtually no RAM; it reads and writes all the sequences at each iteration, sorting them incrementally by digit, wherein the RAM it uses is independent of the number of input sequences. Such a system places more demand on the hard drive and even though efficiency is increased over prior art algorithms, use of a solid state hard drive (SSD) further enhances efficiency of the disclosed algorithms. For example, if a program is running at 80% efficiency on a particular computer system (i.e. with a non-solid state hard drive) then the system is wasting 20% of its time doing nothing but waiting for the hard drive to provide more data; clearly not an ideal system. The disclosed use of SSD drives, super fast hard drives based on flash memory instead of physically spinning magnetic disks bypasses the communication inefficiencies of the typical hard drive thereby increasing the efficiency of the whole system. As such, the disclosed algorithms and their methods of use improve the efficiency of current reporting systems, for example real world time-to-result, by minimizing the number of bytes of data that must be read from, and written to, the hard drive.

Algorithm3 builds on the foundations of algorithm1 and algorithm2. Text data is often stored using 8 bits per character (i.e., ASCII code). Since DNA data contains typically 4 characters (i.e., A, C, T and G) a code can be used that takes up fewer bits/character; DNA data can fit into 2 bits/base but for practical reasons 4 bits/base are used. Using code that takes up fewer bits/character halves the amount of space taken up by the sequences. Using code that takes up fewer bits/character can also be applied to algorithm1 and algorithm2. Second, sequences are processed from right to left. For example, if a 100-base sequence is at iteration 40, one only need copy the 60 characters of each sequence that are still to be processed as the algorithm need not look at the first 40 again so there is no need to copy them. However, at each iteration instead of copying the whole sequence, algorithm3 copies only the prefix of the sequence that is yet to be processed. Averaged over the whole algorithm, this again halves the read and write time associated with the sequences. At each iteration algorithm3 takes the partial BWT string produced by the previous iteration and augments, builds or updates it for compression to the strings instead of storing them as ASCII files resulting in even greater system efficiency. Algorithms1 and 2 can also be modified to incorporate fewer bits/character and its use here is meant to exemplify its incorporation by describing such in context of algorithm3.

The algorithms disclosed herein represent important practical tools for use in computer implemented methods and systems designed to process vast collections of data sets that are generated by modern DNA sequencers. In addition to their effectiveness on very large datasets, a further aspect of practical relevance is that the transformations as described herein are reversible. This is especially important if one wants to use the (compressed) BWT as an archival format that allows extraction of the original strings. One embodiment is to define a permutation π on bwt(S) and F, that represents the symbols of bwt(S) in lexicographic order. One is able to decompose the permutation π into disjoint cycles: $\pi = \pi_1 \pi_2 \ldots \pi_m$. Each cycle $\pi_i$ corresponding to a conjugacy class of a string in S. One can delete any string S in S and obtain the BWT of S\{S}. In both cases, there is no need to construct the BWT from scratch.

Further, algorithm1 provides a degree of parallelization. The computation of the new positions is independent of each other and is thus easily parallelizable. Inserting the new symbols into the partial BWTs can be performed in parallel as well. This allows for the use of multiple processors on multi-core servers while keeping the computational requirements low.

In some embodiments, disclosed herein are strategies for computing a modified BWT string that is even more amenable to compression by second-stage compression techniques. The strategies disclosed herein, referred to as compression-boosting strategies or methods, comprise the reordering or implicit sorting of the strings in a collection of strings in a manner that enables greatly improved compression (second stage compression) over methods that do not employ one of the compression-boosting strategies. The compression boosting methods can be utilized in conjunction with, and incorporated into, algorithm1, algorithm2 and algorithm3 as well as any BWT algorithm. In one embodiment, a strategy for compression-boosting comprises searching for regions termed "SAP-intervals" (SAP standing for "same-as-previous") within the BWT string. The ordering of symbols within a SAP-interval can be changed—when the BWT is inverted this changes the order of the strings in the collection but leaves the strings themselves unaffected. The BWT construction algorithm can be modified to (at minimal additional computational cost) additionally output a bit array termed the "SAP-array" that denotes the boundaries of these intervals. A simple final stage then makes a single pass through the unmodified BWT string and the SAP-array and produces a modified BWT string in which the symbols within SAP-intervals have been permuted so as to make the modified BWT string more amenable to compression. This is herein referred to as a "same-as-previous" or SAP array strategy. In another embodiment, a strategy for compression boosting comprises sorting the strings in the collection such that the reverses of the strings are in lexicographic (also known as alphabetical) order, herein referred to as "reverse lexicographic order" or RLO strategy. For example, the string ACG is lexicographically less then the string TAA, but when placed in RLO-order the string TAA comes first, since its reverse AAT is lexicographically less than the reverse of ACG, which is GCA. Both strategies provide a modified BWT which is more compressible by second-stage compression algorithms compared to methods that do not employ a compression boosting method.

To understand how a BWT string might be compressed, a string can be thought of as a concatenation of a set of "runs" of, for example, like letters each of which can be described by its constituent symbol c plus an integer i denoting the number of times c is repeated. If all runs in this example are maximal runs (e.g., a run does not abut another run of the same character), then for two strings of the same length it is contemplated that the string that consists of fewer, and on average longer, runs to compress to a smaller size.

Given S, one embodiment for reordering a sequence is to search for permutations S→S' of the sequences in the collection such that the BWT of the permuted collections S' can be more readily compressed than the BWT of S. For the BWT of S, methods disclosed herein describe a bit array called the "Same as Previous" or "SAP" array. Elements of the SAP array are set to 1 if and only if the suffixes associated with their corresponding characters in the BWT are identical (their end markers excluded) to those associated with the characters that precede them. Thus, each 0 value in the SAP array denotes the start of a new SAP interval in the BWT, within which the new SAP interval all characters share an identical associated suffix.

The BWT of S and S' can only differ within SAP intervals that contain more than one distinct symbol. Within such a SAP interval, the ordering of the characters is determined by the ordering of the reads in which they are contained, with best compression achieved if the characters are permuted such that they are grouped into as few runs as possible. As such, in one embodiment the sequences in the collection are implicitly permuted.

Another embodiment for reordering a sequence is illustrated in FIG. 4, wherein a collection of characters in a data string is sorted such that the reverses of the sequences are in lexicographic order (reverse lexicographic order or RLO) such that the symbols in a SAP interval of length l group into at most r runs, where $r \leq \sigma$ is the number of distinct characters encountered within the interval. This compares with an upper round up to l runs if no sorting is applied. It was contemplated that the RLO sorting of a collection would compress better than the original collection of characters. This expectation was determined to be the case when applying the disclosed methods to experimental data derived from E. coli and human genomic data sets (Examples 3 and 4).

In some embodiments, it would be preferential to avoid sorting the collection as a preprocessing step. As such, in one embodiment wherein the SAP array of a BWT is determined both the BWT and its SAP array are read in tandem, SAP intervals are identified, characters sorted and a modified BWT is output. A skilled artisan will understand that latitude exists for employing different heuristics. For example, in FIG. 4 placing the T prior to the two Gs in the ACCT interval would eliminate another run by extending the run of Ts begun in the preceding ACCACT interval thereby further refining the methods.

It remains to compute the SAP-array. In embodiments disclosed herein, the method of BWT construction (i.e., algorithm1, algorithm 2 and algorithm3) can be modified to compute the SAP-array alongside the BWT with minimal additional overhead. As disclosed herein, the BWT construction algorithms proceed in k stages, k being the length of the reads in the collection. At stage j, the j-suffixes ($0 \leq j \leq k$) of the reads (e.g., the suffixes of length j, the 0 suffix being defined as the suffix that contains only the end marker $) are processed in lexicographic order and the characters that proceed them are merged into a partial BWT.

The partial BWT at step j can be thought of as the concatenation of $\sigma 1$ segments $B_j(0), B_j(1), \ldots, B_j(\sigma)$, where each $B_j(h)$ corresponds to the symbols in the partial BWT segments that precede all suffixes of S that are of length smaller or equal to j starting with $c_0=\$$, for $h=0$, and with $c_h \in \Sigma$, for $h=1, \ldots, \sigma$.

At each step j, with $0 < j \leq k$ the positions of all characters that precede the j-suffixes in the old partial BWT are computed in order to obtain an updated partial BWT that also contains the symbols associated with the suffixes of length j.

The algorithms disclosed herein (algorithm1, algorithm2, algorithm3) contrive in slightly different ways (e.g., with different tradeoffs between RAM usage, I/O, etc.) to arrange matters so that the symbols to insert into the partial BWT are processed by lexicographic order of their associated j-suffixes, which allows each segment of the partial BWT to be held, for example, on disk and accessed sequentially. Moreover, this means that the characters in a SAP-interval will be processed consecutively. As such, when a BWT character is written its SAP status can be written at the same time since it will not change in subsequent iterations.

For example, consider two suffixes u and v of length j of two different reads $s_r$ and $s_t$ satisfying $1 \leq r$, $t \leq m$ and $r \neq t$. Both $s_r$ and $s_t$ belong to S and assume that u is lexicographically less than v. In this example, the two reads are identical up to the end markers and as such the SAP status of v must be set to 1 if and only if the following conditions hold: the symbols associated with suffixes u' and v' of length (j−1) of $s_r$ and $s_t$ are equal which guarantees that u and v begin with the same symbol, and they are stored in the same BWT segment, implying that u' and v' begin with the same symbol. The SAP status of all suffixes between u' and v' must be set to 1 which ensures that all suffixes between u' and v' in iteration j−1 coincide and have the length j−1. It is noted that the symbols in the BWT segment associated with suffixes between u' and v' could be different from the symbol preceding u' (and v').

Continuing with the example, the SAP status of the suffixes u and v are computed at step j−1 when the corresponding suffixes u' and v' are inserted. In particular, when the values from the old to the new partial BWT are copied and inserted into the new m values, the SAP values can be read and the aforementioned conditions can be verified at the same time. As such, at the end of the iteration j−1 the partial BWT and the SAP values of the next suffixes to insert are obtained and, at iteration j, the SAP status of the j-suffixes can be set and the SAP status of the suffixes of the next iteration can be computed.

Further, the SAP interval can be computed by induction, for example the SAP status of the j-suffixes at iteration j−1 can be computed by using the symbols associated with the (j−1) suffixes and their SAP values. For example, at iteration j−1, it is contemplated that the SAP values of the (j−1) suffixes are known and the SAP values of the j-suffixes needed for the next iteration are computed. For simplicity, when focusing on the computation of the SAP values of a fixed BWT segment, for example the insertion of the (j−1) suffixes starting with the same symbol can be considered.

To continue with the example, a counter A for each symbol of the alphabet and a generic counter Z are described. The element A[h], for each h=1, ..., σ and $c_h \epsilon \Sigma$ contains the number of SAP intervals between the first position and the position of the last inserted symbol associated with a read $s_q$ (for some 1≤q≤m) equal to $c_h$ in the considered BWT segment. In this example, the end markers are ignored because the reads have the same length and hence it does not appear in the partial BWT. The counter Z contains the number of the SAP intervals between the first position and the position where $c_p$ is inserted. The symbol $c_p$ is associated with the new suffix of length j−1 of read $s_t$, with 1≤t≤m. If the value A[p] is equal to Z, then the SAP status of the j-suffix of $s_t$ (obtained by concatenating $c_p$ (j−1) suffix of $s_t$) must be set to 1, otherwise it is set to 0. It was detemined that if A[p]=Z holds true then this implies that j-suffixes of $s_r$ and $s_t$ are in the same SAP interval.

As such, strategies are disclosed herein for the lossless compression of a large amount of data that can result, for example from an experiment such as a DNA sequencing experiment wherein a large number of short DNA sequence reads result in large amounts of raw data.

The present disclosure provides embodiments directed at computer implemented methods and systems for analysis of datasets, in particular large datasets for example datasets of at least 25 million characters, at least 50 million characters, at least 100 million characters, at least 500 million characters, at least 750 million characters, at least 1 billion characters, at least 10 billion characters, at least 50 billion characters, at least 100 billion characters, at least 1 trillion or terabase characters, at least 10 trillion characters, at least 50 trillion characters, or at least 100 trillion characters. Certain illustrative embodiments of the invention are described below. The present invention is not limited to these embodiments.

In some embodiments, computer implemented methods and systems comprising algorithms as described herein are used in methods and systems for enhanced error correction, for example enhanced to that provided by use of a k-mer table. In some embodiments, computer implemented methods and systems comprising algorithms as described herein can be used for a myriad of applications that would benefit from increased efficiencies in data compression, greater efficiencies in terms of data storage and usage and greater efficiencies in time including, but not limited to, de novo sequence assembly, comparison of test genome sequences to those of reference genomic sequences, determining the presence or absence of SNVs, insertions, deletions, SNPs and other genomic variant mutations in a genome, comparing test RNA sequences to those of reference RNA sequences, determining splice variants, RNA sequence anomalies, presence or absence of RNA sequences, resequencing of a genome, linguistic related areas of research such as tracking language evolution over time, incorporation into computer search engines for more expedient text searching, etc. Advantages of practicing the methods and systems as described herein can provide investigators with more efficient systems that utilize fewer computer resources while maximizing data analysis time, thereby providing investigators with additional tools for determining the presence or absence of disease related genomic anomalies which may be used by a clinician to diagnose a subject with a disease, to provide a prognosis to a subject, to determine whether a patient is at risk of developing a disease, to monitor or determine the outcome of a therapeutic regimen, and for drug discovery. Further, information gained by practicing computer implemented methods and systems comprising algorithms as described herein finds utility in personalized healthcare initiatives wherein an individual's genomic sequence may provide a clinician with information unique to a patient for diagnosis and specialized treatment. Therefore, practicing the methods and systems as described herein can help provide investigators with answers to their questions in shorter periods of time using less valuable computer resources.

In some disclosed embodiments, methods and systems are provided for computational analysis of data sets, in particular large data sets for example datasets of at least 25 million characters, at least 50 million characters, 100 million characters, at least 500 million characters, at least 750 million characters, at least 1 billion characters, at least 10 billion characters, at least 50 billion characters, at least 100 billion characters, at least 1 trillion or terabase characters, at least 10 trillion characters, at least 50 trillion characters, or at least 100 trillion characters utilizing computer implemented methods and systems comprising algorithms as described herein. In some embodiments, methods and systems are provided for computational analysis of large data sets generated by sequencing a genome. Accordingly, disclosed embodiments may take the form of one or more of data analysis systems, data analysis methods, data analyses software and combinations thereof. In some embodiments, software written to perform methods as described herein is stored in some form of computer readable medium, such as memory, CD-ROM, DVD-ROM, memory stick, flash drive, hard drive, SSD hard drive, server, mainframe storage system and the like. A skilled artisan will understand the basics of computer systems, networks and the like, additional information can be found at, for example, Introduction to Computing Systems (Pat and Patel, Eds., 2000, $1^{st}$ Ed., McGraw Hill Text), Introduction to Client/Server Systems (1996, Renaud, $2^{nd}$ Edition, John Wiley & Sons), both of which are incorporated herein by reference in their entireties.

Computer software products comprising computer implemented methods comprising algorithms as described herein may be written in any of various suitable programming languages, for example compiled languages such as C, C#, C++, Fortran, and Java. Other programming languages could be script languages, such as Perl, MatLab, SAS, SPSS, Python, Ruby, Pascal, Delphi, R and PHP. In some embodiments, the computer implemented methods comprising the algorithms as described herein are written in C, C#, C++, Fortran, Java, Perl, R, Java or Python. In some embodiments, the computer software product may be an independent application with data input and data display modules. Alternatively, a computer software product may include classes wherein distributed objects comprise applications including computational methods as described herein. Further, computer software products may be part of a component software product for determining sequence data including, but not limited to, computer implemented software products associated with sequencing systems offered by Illumina, Inc. (San Diego, Calif.), Applied Biosystems and Ion Torrent (Life Technologies; Carlsbad, Calif.), Roche 454 Life Sciences (Branford, Conn.), Roche NimbleGen (Madison, Wis.), Cracker Bio (Chulung, Hsinchu, Taiwan), Complete Genomics (Mountain View, Calif.), GE Global Research (Niskayuna, N.Y.), Halcyon Molecular (Redwood City, Calif.), Helicos Biosciences (Cambridge, Mass.), Intelligent Bio-Systems (Waltham, Mass.), NABsys (Providence, R.I.), Oxford Nanopore (Oxford, UK), Pacific Biosciences (Menlo Park, Calif.), and other sequencing software related products for determining sequence from a nucleic acid sample.

In some embodiments, computer implemented methods utilizing algorithms as described herein may be incorporated into pre-existing data analysis software, such as that found on sequencing instruments. An example of such software is the CASAVA Software program (Illumina, Inc., see CASAVA Software User Guide as an example of the program capacity, incorporated herein by reference in its entirety). Software comprising computer implemented methods as described herein are installed either onto a computer system directly, or are indirectly held on a computer readable medium and loaded as needed onto a computer system. Further, software comprising computer implemented methods described herein can be located on computers that are remote to where the data is being produced, such as software found on servers and the like that are maintained in another location relative to where the data is being produced, such as that provided by a third party service provider.

Output of practicing the computational methods as described can be via a graphic user interface, for example a computer monitor or other display screen. In some embodiments, output is in the form of a graphical representation, a web based browser, an image generating device and the like. In some embodiments, a graphical representation is available to a user at any point in time during sequencing data acquisition, for example after one cycle, five cycles, 10 cycles, 20 cycles, 30 cycles thereby providing a user a graphical representation of the sequence of interest as the sequencing reaction progresses, sequence that is based on the incremental building of the BWT as described herein. However, in some embodiments output can be in the form of a flat text file that contains sequence information, wherein the text file is added to for each subsequent cycle thereby providing a text file reporting of the sequence of interest as the sequencing reaction progresses. In other embodiments, output is a graphical and/or flat text file that is assessed at the end of a sequencing analysis instead of at any point during a sequencing analysis. In some embodiments, the output is accessed by a user at any point in time during or after a sequencing run, as it is contemplated that the point during a reaction at which the output is accessed by the user does not limit the use of the computational methods comprising the disclosed algorithms. In some embodiments, output is in the form of a graph, picture, image or further a data file that is printer, viewed, and/or stored on a computer readable storage medium.

In some embodiments, outputting is performed through an additional computer implemented software program that takes data derived from a software program and provides the data as results that are output to a user. For example, data generated by a software program such as CASAVA is input, or accessed, by a sequence analysis viewer, such as that provided by Illumina, Inc. (Sequencing Analysis Viewer User Guide). The viewer software is an application that allows for graphical representation of a sequencing analysis, quality control associated with said analysis and the like. In some embodiments, a viewing application that provides graphical output based on practicing the computational methods comprising the algorithms as described herein is installed on a sequencing instrument or computer in operational communication with a sequencing instrument (e.g., desktop computer, laptop computer, tablet computer, etc.) in a proximal location to the user (e.g., adjacent to a sequencing instrument). In some embodiments, a viewing application that provides graphical output based on practicing the computational methods comprising the algorithms as described herein is found and accessed on a computer at a distant location to the user, but is accessible by the user be remote connection, for example Internet or network connection. In some embodiments, the viewing application software is provided directly or indirectly (e.g., via externally connected hard drive, such as a solid state hard drive) onto the sequencing instrument computer.

FIG. 1 illustrates an exemplary computer system that may be used to execute the computer implemented methods and systems of disclosed embodiments. FIG. 1 shows an exemplary assay instrument (10), for example a nucleic acid sequencing instrument, to which a sample is added, wherein the data generated by the instrument is computationally analyzed utilizing computer implemented methods and systems as described herein either directly or indirectly on the assay instrument. In FIG. 1, the computer implemented analysis is performed via software that is stored on, or loaded onto, an assay instrument (10) directly, or on any known computer system or storage device, for example a desktop computer (20), a laptop computer (40), or a server (30) that is operationally connected to the assay instrument, or a combination thereof. An assay instrument, desktop computer, laptop computer, or server contains a processor in operational communication with accessible memory comprising instructions for implementation of the computer implemented methods as described herein. In some embodiments, a desktop computer or a laptop computer is in operational communication with one or more computer readable storage media or devices and/or outputting devices (50). An assay instrument, desktop computer and a laptop computer may operate under a number of different computer based operational languages, such as those utilized by Apple based computer systems or PC based computer systems. An assay instrument, desktop and/or laptop computers and/or server system further provides a computer interface for creating or modifying experimental definitions and/or conditions, viewing data results and monitoring experimental progress. In some embodiments, an outputting device may be a graphic user interface such as a computer monitor or a computer screen, a printer, a hand-held device such as a personal digital assistant (i.e., PDA, Blackberry, iPhone), a tablet computer (e.g., iPAD®), a hard drive, a server, a memory stick, a flash drive and the like.

A computer readable storage device or medium may be any device such as a server, a mainframe, a super computer, a magnetic tape system and the like. In some embodiments, a storage device may be located onsite in a location proximate to the assay instrument, for example adjacent to or in close proximity to, an assay instrument. For example, a storage device may be located in the same room, in the same building, in an adjacent building, on the same floor in a building, on different floors in a building, etc. in relation to the assay instrument. In some embodiments, a storage device may be located off-site, or distal, to the assay instrument. For example, a storage device may be located in a different part of a city, in a different city, in a different state, in a different country, etc. relative to the assay instrument. In embodiments where a storage device is located distal to the assay instrument, communication between the assay instrument and one or more of a desktop, laptop, or server is typically via Internet connection, either wireless or by a network cable through an access point. In some embodiments, a storage device may be maintained and managed by the individual or entity directly associated with an assay instrument, whereas in other embodiments a storage device may be maintained and managed by a third party, typically at a distal location to the individual or entity associated with an assay instrument. In embodiments as described herein, an outputting device may be any device for visualizing data.

In embodiments as described herein, an assay instrument, desktop, laptop and/or server system may be used itself to store and/or retrieve computer implemented software programs incorporating computer code for performing and implementing computational methods as described herein, data for use in the implementation of the computational methods, and the like. One or more of an assay instrument, desktop, laptop and/or server may comprise one or more computer readable storage media for storing and/or retrieving software programs incorporating computer code for performing and implementing computational methods as described herein, data for use in the implementation of the computational methods, and the like. Computer readable storage media may include, but is not limited to, one or more of a hard drive, a SSD hard drive, a CD-ROM drive, a DVD-ROM drive, a floppy disk, a tape, a flash memory stick or card, and the like. Further, a network including the Internet may be the computer readable storage media. In some embodiments, computer readable storage media refers to computational resource storage accessible by a computer network via the Internet or a company network offered by a service provider rather than, for example, from a local desktop or laptop computer at a distal location to the assay instrument.

In some embodiments, computer readable storage media for storing and/or retrieving computer implemented software programs incorporating computer code for performing and implementing computational methods as described herein, data for use in the implementation of the computational methods, and the like is operated and maintained by a service provider in operational communication with an assay instrument, desktop, laptop and/or server system via an Internet connection or network connection.

In some embodiments, an assay instrument is an analysis instrument including, but not limited to, a sequencing instrument, a microarray instrument, and the like. In some embodiments, an assay instrument is a measurement instrument, including but not limited to, a scanner, a fluorescent imaging instrument, and the like for measuring an identifiable signal resulting from an assay.

In some embodiments, an assay instrument capable of generating datasets for use with computer implemented methods as described herein, as such assays instruments that comprise computer implemented systems as described herein, include but are not limited to, sequencing assay instruments as those provided by Illumina®, Inc. (HiSeq 1000, HiSeq 2000, Genome Analyzers, MiSeq, HiScan, iScan, BeadExpress systems), Applied Biosystems™ Life Technologies (ABI PRISM® Sequence detection systems, SOLiD™ System), Roche 454 Life Sciences (FLX Genome Sequencer, GS Junior), Applied Biosystems™ Life Technologies (ABI PRISM® Sequence detection systems, SOLiD™ System), Ion Torrent® Life Technologies (Personal Genome Machine sequencer) further as those described in, for example, in United States patents and patent applications U.S. Pat. Nos. 5,888,737, 6,175,002, 5,695,934, 6,140,489, 5,863,722, 2007/007991, 2009/0247414, 2010/0111768 and PCT application WO2007/123744, each of which is incorporated herein by reference in its entirety. Methods and systems disclosed herein are not necessarily limited by any particular sequencing system, as the computer implemented methods comprising algorithms as described herein are useful on any datasets wherein alignment procedures and processes are practiced.

Computer implemented methods and systems comprising algorithms as described herein are typically incorporated into analysis software, although it is not a prerequisite for practicing the methods and systems described herein. In some embodiments, computer implemented methods and systems comprising algorithms described herein are incorporated into analysis software to analyzing sequencing datasets, for example software programs such as Pipeline, CASAVA and GenomeStudio data analysis software (Illumina®, Inc.), SOLiD™, DNASTAR® SeqMan® NGen® and Partek® Genomics Suite™ data analysis software (Life Technologies), Feature Extraction and Agilent Genomics Workbench data analysis software (Agilent Technologies), Genotyping Console™, Chromosome Analysis Suite data analysis software (Affymetrix®).

Figure 2B:
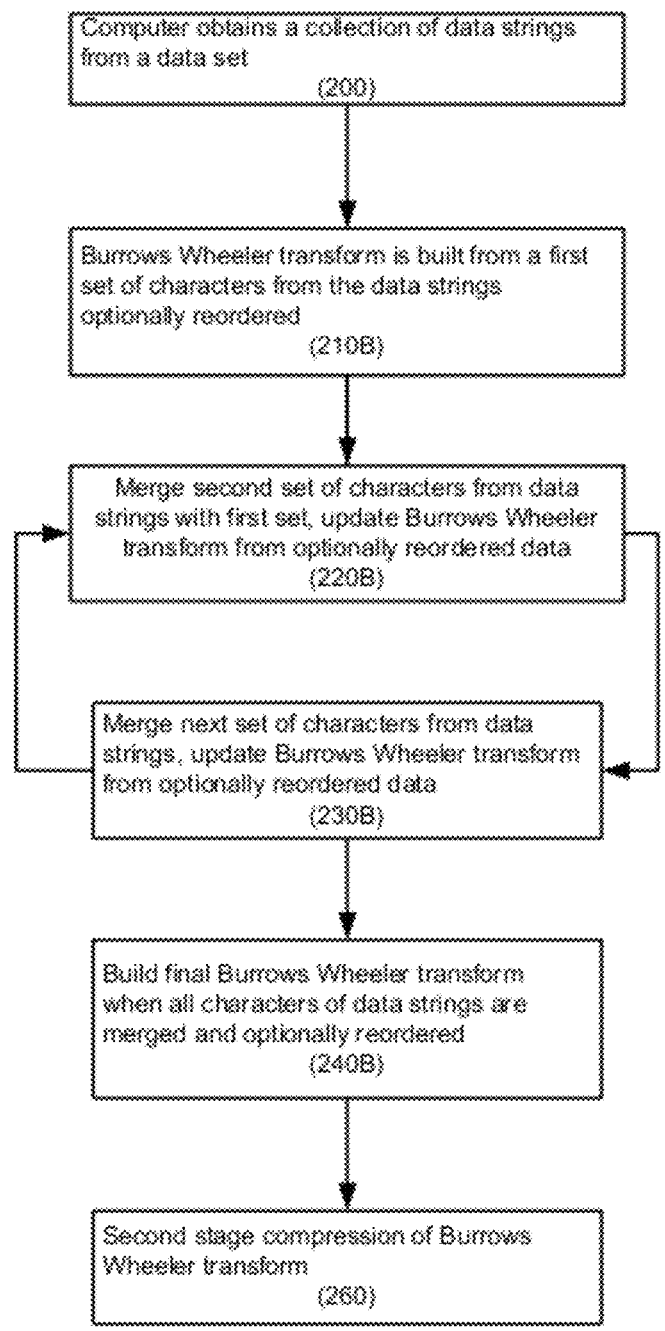

FIG. 2 illustrates the general flow of an embodiment of a computer implemented method. A computer assesses a data set, either from internal memory or as provided by a computer readable storage medium, and a collection of data strings is created (200). The computer selects a first collection of characters from the data set and utilizing algorithm1, 2 or 3 as described herein builds the BWT on the first collection of characters (210). A second collection of characters from the data strings can be merged with the first collection of characters wherein the BWT is augmented or incrementally built to include the newly merged collection of characters (220). The method of merging additional sets of characters and augmenting or building the BWT (230) proceeds incrementally, character by character, until all the sets of characters that make up the data strings are merged, wherein the BWT is determined for the complete data set (240). At any point in time during the merging of characters and BWT augmenting, one or more additional data sets can be added to the process, further one or more data sets can be removed from the process. Additionally, a compression boosting method can be employed for resordering the input data to increase compression over BWT alone. In one method (FIG. 2A-205) the BWT algorithm can be modified to resort the data by practicing the reverse lexicographic reordered (RLO) compression boosting method prior to building the BWT. In another embodiment, reordering of data can be performed by modifying the BWT algorithm to concurrently resort the data and build the BWT following the same as previous (SAP) compression boosting method (FIG. 2B). Employing either compression boosting method creates a data set that is more compressed and therefore more compressible by second stage compression methods (260) than compressing a BWT based on a data set that was not reordered. Once the BWT is built it can be compressed by second stage compression methods (260). Second stage compression methods include, but are not limited to, bzip2, ReCoil, GenCompress, 7-zip, gzip, etc.

Preferably, reordering is performed by practicing one of the algorithms that has been modified to incorporate one of the compression boosting methods disclosed herein in addition to that which is already present in the algorithm. For example, reordering using the SAP or RLO strategies concurrent with or prior to building the BWT of a data set results in a more compressed data set for second stage compression compared to compression which occurs by practicing algorithm1, algorithm2 or algorithm3 without the compression boosting modifications.

A data set that is accessed by a computer to build a collection of data strings can be from any source, such as nucleic acid sequence data, amino acid sequence data, written documents, image derived data, and the like. Example 1 demonstrates the incremental merging of data characters followed by BWT augmentation when utilizing nucleic acid sequence data as the data set.

The previously described sequence data analysis comprising computer implemented methods as described herein can be performed on an assay instrument proper, on a computer system in operational communication with an assay instrument, either proximal or distal to the assay instrument. In some embodiments, computer implemented methods as described herein can generate comparative matches of at least 1000 matches/second, at least 2000 matches/second, at least 3000 matches/second, at least 5000 matches/second or at least 10000 matches/second.

In some embodiments, a hardware platform for providing a computational environment comprises a processor (i.e., CPU) wherein processor time and memory layout such as random access memory (i.e., RAM) are systems considerations. For example, smaller computer systems offer inexpensive, fast processors and large memory and storage capabilities. In some embodiments, hardware platforms for performing computational methods as described herein comprise one or more computer systems with one or more processors. In some embodiments, smaller computer are clustered together to yield a supercomputer network (i.e., Beowulf clusters), which may be preferential under certain circumstances as a substitute for a more powerful computer system. Indeed, computational methods as described herein are particularly suited to a smaller computer system where limited RAM exists.

In some embodiments, computational methods as described herein are carried out on a collection of inter- or intra-connected computer systems (i.e., grid technology) which may run a variety of operating systems in a coordinated manner. For example, the CONDOR framework (University of Wisconsin-Madison) and systems available through United Devices are exemplary of the coordination of multiple stand alone computer systems for the purpose dealing with large amounts of data. These systems offer Perl interfaces to submit, monitor and manage large sequence analysis jobs on a cluster in serial or parallel configurations.

In some embodiments, a computer implemented method comprising an algorithm as described herein is used to determine the sequence of a nucleic acid sample (e.g., a genomic DNA sample). In some embodiments, a computer implemented method comprising an algorithm as described herein is implemented upon completion of a sequencing assay. In embodiments of the present disclosure, computer implemented methods and software that comprises those methods are found loaded onto a computer system or are located on a computer readable media that is capable of being accessed and processed by a computer system. For example, computer implemented methods as described herein can read rows of sequences in their entireties and input characters from the rows into algorithms as described herein that are implemented in a computer implemented method. The computer implemented algorithm can split the rows into columns; each retained in a unique file, and computes the BWT for the set of sequences. A reference, or query sequence (e.g., a reference genome of interest) can be provided. The computed BWT for the target sequence can be compared to the reference genome of interest, for example, and the comparative results outputted to the user via a, for example, graphic user interface such as a computer monitor, tablet computer, and the like. Comparative results can also be outputted to a storage device, computer readable storage media, printer, and the like for storage or preservation of the results of said comparison. Such comparative results can also be examined for target sequence anomalies such as single nucleotide variants or polymorphisms, sequence insertions and/or deletions, and other genomic derived information. As such, the computer implemented methods comprising algorithms as described herein can provide genetic information used in, for example, determining or diagnosing the presence of a disease state or condition in a subject, prognosing risk for a subject of developing a disease or condition, monitoring a therapeutic treatment regimen of a subject, prognosing therapeutic success of a patient, determining the risk for a subject with regards to developing a particular disease or condition, and the like. Indeed, computer implemented methods and systems comprising an algorithm as described herein can put crucial sequence data in the hands of clinicians in a more efficient manner than is currently available.

In some embodiments, the computer implemented method comprising algorithm1 determines the sequence of a nucleic acid sample during sequence analysis or once sequence analysis is complete. For example, a computer implemented method comprising algorithm1 determines a nucleic acid sequence following the completion of each cycle in a sequencing cycle. For example with regards to sequence by synthesis technologies, each sequence cycle determines which of four nucleotides, A, C, G or T is incorporated at that particular location, thereby defining the base that is the complement of that being sequenced (e.g., A is complementary to T, C is the complement of G). Typically, computational analysis of a target sequence occurs once all the sequencing cycles have completed for a target sequence which requires a large amount of computer RAM for short term storage of the accumulating data prior to final sequence determination.

Additionally, a computer implemented method comprising algorithm1 analyzes data in a real time fashion by incrementally building the BWT files at any point during a sequence assay, for example at cycle 10, 15, 20, etc. Such an application could provide an investigator with a visual output (e.g., via graphic user interface) at any time during a sequencing assay thereby allowing an investigator to monitor a sequencing assay, view sequencing results, utilize partial sequencing results for additional operations, etc. at any given point during a sequencing assay. Further, implementation of a computer method comprising algorithm1 utilizes minimal to no RAM, as such its implementation can be performed on a computer with typically relatively small quantities of RAM, such as a standard desktop computer, laptop computer system, tablet computer, and the like.

In particular embodiments, the BWT of a collection of strings has two important practical properties; reversibility such that if a BWT of a string is known one can reconstruct the original dataset and the BWT of a string is more amenable to compression than the original dataset as the BWT tends to group identical characters together. These two BWT properties provide for a method that results in a lossless compression of a string dataset. The popular open source lossless data compression algorithm "bzip2" has a similar compression property (available through Berkeley Software Distribution, University of California Berkeley). A third property of particular embodiments of the BWT is that it facilitates the efficient computation of the two operations occ(X) and locate (X). The operation occ(X) computes the frequency at which a string (X) occurs in a data dataset, for example it might compute that string AACG occurs three times in a dataset. The operation locate(X) computes the location of a string (X) in a dataset, for example string AACG occurs at position 12 in sequence 338, at position 3 in sequence 1408 and at position 57 in sequence 1501.

In some embodiments, computer implemented methods comprising algorithms described herein for computing BWT allows for the efficient computation of the two operations occ(X) and locate(X) on large datasets for comparative sequence analysis. For example, computer implemented methods as described herein can be used to compare two related sets of string data collections and, using occ(X) and locate(X), determine the differences between them. For example, for a genomic sequence that is sequenced to 30 fold redundancy (e.g., each position in the target sequence is, on average, sampled and sequenced 30 times), computer implemented methods as described herein can be applied and occ (X) queries can be used to search the sequences for strings that occurs a significant number of times in one sequence dataset relative to the comparative sequence dataset.

An example of such comparative analysis resulting from practicing the computer implemented methods as described herein finds utility in determining and/or diagnosing the presence or absence of a tumor or disease state in a subject. Cancer is caused by damage to cellular DNA, leading to uncontrolled cellular proliferation and tumor formation. It is, therefore, important to determine how DNA of cancer cells may differ from DNA found in normal, non-cancerous cells. A typical process for determining such differences is to compare a set of DNA sequences derived from tumor cells with that from DNA sequences derived from no-tumor cells from the same individual. Such a comparison can be accomplished by analyzing the tumor DNA sequences and the non-tumor DNA sequences by standard methods for detecting variants, for example by aligning the sequences to a standard reference dataset (e.g., such as that found publically available through the UCSC Genome Browser created by the Genome Bioinformatics Group of University of California Santa Cruz), followed by post-processing steps to identify various types of differences between the sample and the reference (e.g., single nucleotide variants, insertions and/or deletions, etc.). In this scenario, variants found in the non-tumor DNA can be subtracted from the variants identified in the tumor DNA, thereby identifying somatic mutations that are present only in the tumor DNA.

However, in lieu of utilizing such comparative and subtractive methods, computer implemented methods as described herein can be implemented to compare tumor and non-tumor DNA. In an exemplary embodiment, BWTs can be created for both tumor and non-tumor DNA derived from tissues obtained from a subject having chronic lymphocytic leukemia (CLL). In this example, sequences that align to the human reference genomic sequence are excluded in order to reduce the complexity of the final comparison, as such homologous sequence are less likely to be somatic variants. However, as computer implemented methods described herein find particular utility in analyzing large data sets, this reduction of complexity is not required. In the present scenario, all tumor sequences are split into at least 31 base pair fragments or larger, as it is contemplated that fragments of this size or larger have a reasonably good chance of being unique in a sampled genome. As sequence can be derived from both stands of the DNA double helix, sequence from both strands, X and its reverse complement X', are queried to obtain an overall abundance of strand X. All X wherein occ(X)+occ(X) was greater than 8 was extracted in the tumor DNA (an arbitrary number used for purposes of this example) as well as all X wherein occ(X)+occ(X) was zero (i.e., X that was absent from the tumor DNA dataset). Following the initial extractions, 31-mers are assembled into longer sequences utilizing, for example the publically available Velvet assembly tool. The assembled sequences are then aligned to the reference genome sequence using, for example, the publically available BLAT alignment program, thereby determining the somatic variations present in the tumor DNA from the subject.

Additionally, handling of the list of tumor only k-mers can be refined in a number of ways. For example, all sequences could be assembled that contain tumor only k-mers, thereby obtaining assembled sequences that feature not only the tumor only sequences, but also the surrounding sequence. Such an assembly could provide for enhanced genomic mapping. Further, if "paired" DNA sequencing is performed, a typical procedure known in the art, then the paired or partner sequence reads can all be input into the assembly process, which provides an additional aide in determining somatic variants in a tumor DNA genome.

In some embodiments, comparative analysis implementing computer methods comprising algorithms as described herein are used in performing the BWT for comparing genome to transcriptome data sets. In eukaryotes, genomic DNA is transcribed into RNA, which can in turn be transcribed back into cDNA by the enzyme reverse transcriptase, which can in turn be sequenced. Sequencing of the reverse transcribed RNA is commonly referred to as RNA sequencing or RNASeq. Genomic and RNASeq data sets from the same subject can be compared by creating the BWT of each data set using computer implemented methods as described herein, and using the occ(X) queries to identify sequence fragments present in the RNASeq data but absent in the genomic dataset. Such sequence identification may identify important intron/exon boundaries which is important in determining gene structure and the like. Determining gene structure is useful, for example, when an organismal related reference sequence is not yet available or is only of a preliminary or draft-like quality.

In some embodiments, computer implemented methods described herein for computing the BWT of a dataset is used in determining de novo mutations in a genome. For example, a common experimental design in genetic family determinations involves sequencing members of a family, such as parents, children, aunts, uncles, etc. The overwhelming majority of a child's DNA will come from one or the other parent. However, there will also typically be a small amount of de novo mutation, or sequence variants or polymorphisms that are not derived from one or the other parent. By practicing the computer implemented methods as described herein, the BWT of child derived sequences can be created and compared to the BWT created from a combination of sequences from one or both parents. The occ(X) can then be applied to identify sequences present in the child which are not present in one or both of the parents.

In some embodiments, computer implemented methods as described herein for computing the BWT of a dataset can be used for archiving a subject genomic data in a more compressed and efficient manner. For example, the BWT derived from computer implemented methods described herein could provide archival genomic datasets that are stored in a form that are both compressed and indexable. An issue with whole genome sequencing is that genome-wide analysis is problematic when trying to identify a disease related genotype. For example, oftentimes clinician's are only interested in a particular region of the genome, for example a region that is known or suspected of containing a disease related biomarker. As such, a clinician is only interested in analyzing a limited region of the genome and nothing further. Computer implemented methods as described herein could be applied to such a limited region by computing occ(X) and/or locate(X) of only that region without having to analyze a whole genome.

Exemplary embodiments described herein are descriptive of DNA alphabet datasets which may or may not be of constant length. However, methods and systems and described herein are not limited to DNA datasets. Indeed, the methods and systems as described herein are applicable to any dataset. For example, computer implemented methods and systems described herein can be used to process datasets in any other natural language text, such as English and the like. In such a language text, boundaries of strings in the dataset could be set to anything, such as at word boundaries (for example, as discussed in suffix arrays as found at http://www.cs.ucr.edu/~stelo/cpm/cpm07/suffix_array_on_words_ferragina.pdf). Further, boundaries in alternative language text could be placed at the ends of phrases or sentences and the like. Such placement would allow for searching by phrases, or sub-phrases, within sentences by either occ(X) and/or locate(X).

The following examples are provided in order to demonstrate and further illustrate certain preferred embodiments and aspects of the present invention and are not to be construed as limiting the scope thereof.

EXAMPLES

Example 1

Incremental Building of the BWT on a Sequence Dataset

The following workflow is an exemplary description of a computer implemented incremental building or augmenting of the BWT of the three algorithms1, 2 and 3 using algorithm1 as the exemplary algorithm. The data set and associated collection of data strings are derived from a nucleic acid sequence and are for demonstration purposes only as the data sets could derive from a variety of sources as previously described. Further the length of the data strings are 7 nucleotides, but any length or variety of lengths could also be used.

Three sequences of length 7 are as follows:

SeqID 1- TACCAAC

SeqID 2- AAAGCTC

SeqID 3- GTCGCTT

Which correspond to:
0→$
1→A
2→C
3→G
4→N
5→T

All the characters are indexed starting from 0 rather than 1, except the positions in the partial-BWTs that are indexed by 1. As such, the characters of the sequence are indexed from 0 to 6 as follows:

| SeqId | 0 | 1 | 2 | 3 | 4 | 5 | 6 | 7 |
|---|---|---|---|---|---|---|---|---|
| 0 | T | A | C | C | A | A | C | $1 |
| 1 | A | A | A | G | C | T | C | $2 |
| 2 | G | T | C | G | C | T | T | $3 |

Where "$" symbol is a symbol that does not belong to the dataset alphabet, and where all "$" are considered equal, i.e. $1=$2=$3=$.

The first step in the incremental building of the BWT is an initialization step.

Iteration j=0

The characters in position 6 are first considered. The characters in position 6 are concatenated (i.e., the assumption that $1<$2<$3) to give CCT. The following BWT partial files (one for each character of the sequence) of the first step, iteration j=0, are built:
B[0]: CCT
B[1]: empty
B[2]: empty
B[3]: empty
B[4]: empty
B[5]: empty The following vector of triples (Q, P, N) is:

| Q | 0 | 0 | 0 |
|---|---|---|---|
| P | 1 | 2 | 3 |
| N | 0 | 1 | 2 |

Such that:
The character of the sequence 0 has been inserted in the position 1 of the partial BWT 0
The character of the sequence 1 has been inserted in the position 2 of the partial BWT 0
The character of the sequence 2 has been inserted in the position 3 of the partial BWT 0

Iteration j=1
The characters found in position 5 of the sequence data string are now considered. The characters in position 5 are merged or inserted with the symbols in position 6. As such the new characters for merging are ATT.

The vector of triples is:

| Q | 0 | 0 | 0 |
|---|---|---|---|
| P | 1 | 2 | 3 |
| N | 0 | 1 | 2 |

The old partial-BWTs are:
B[0]: CCT
B[1]: empty
B[2]: empty
B[3]: empty
B[4]: empty
B[5]: empty
By reading the following vector of triples (Q, P, N):

| Q | 0 | 0 | 0 |
|---|---|---|---|
| P | 1 | 2 | 3 |
| N | 0 | 1 | 2 |

It is known that:
The character of the sequence 0 has been inserted in the position 1 of the partial BWT 0
The character of the sequence 1 has been inserted in the position 2 of the partial BWT 0
The character of the sequence 2 has been inserted in the position 3 of the partial BWT 0
Updating the vector of triples with the new merged characters from position 5 yields:

| Q | 2 | 2 | 5 |
|---|---|---|---|
| P | 1 | 2 | 1 |
| N | 0 | 1 | 2 |

The vector of triples are sorted from Q to P to N yielding the following vectors:

| Q | 2 | 2 | 5 |
|---|---|---|---|
| P | 1 | 2 | 1 |
| N | 0 | 1 | 2 |

Which can be interpreted as:
The character of the sequence 0 (that is the symbol A is to be inserted in position 1 of the partial BWT 2
The character of the sequence 1 (that is the symbol T) is to be inserted in position 2 of the partial BWT 2
The character of the sequence 2 (that is the symbol T) is to be inserted in position 1 of the partial BWT 5
The new partial-BWTs are built by inserting or merging the characters of position 5 with those of position 6 as defined by the previous sort, such that:
B[0]: CCT
B[1]: empty
B[2]: AT
B[3]: empty
B[4]: empty
B[5]: T
Iteration j=2

The next characters for consideration and incremental merging are those of position 4, as such ACC.
The vector of the triples is:

| Q | 2 | 2 | 5 |
|---|---|---|---|
| P | 1 | 2 | 1 |
| N | 0 | 1 | 2 |

The old partial-BWTs are:
B[0]: CCT
B[1]: empty
B[2]: AT
B[3]: empty
B[4]: empty
B[5]: T
By reading the following vector of triples (Q, P, N):

| Q | 2 | 2 | 5 |
|---|---|---|---|
| P | 1 | 2 | 1 |
| N | 0 | 1 | 2 |

It is known that:
The character of the sequence 0 has been inserted in position 1 of the partial BWT 2
The character of the sequence 1 has been inserted in position 2 of the partial BWT 2
The character of the sequence 2 has been inserted in position 1 of the partial BWT 5
The values in the vector of the triples are updated:

| Q | 1 | 5 | 5 |
|---|---|---|---|
| P | 1 | 2 | 3 |
| N | 0 | 1 | 2 |

After sorting, the vectors are:

| Q | 1 | 5 | 5 |
|---|---|---|---|
| P | 1 | 2 | 3 |
| N | 0 | 1 | 2 |

Which can be interpreted as:
The character of the sequence 0 (that is the symbol A) is to be inserted in the position 1 of the partial BWT 2
The character of the sequence 1 (that is the symbol C) is to be inserted in the position 2 of the partial BWT 2
The character of the sequence 2 (that is the symbol C) is to be inserted in the position 3 of the partial BWT 5
The new partial-BWTs are build by inserting the characters as determined:
B[0]: CCT
B[1]: A B[2]: AT
B[3]: empty
B[4]: empty
B[5]: TCC
Iteration j=3
The symbols in position 3 are now considered, so CGG.
The vector of the triples is:

| Q | 1 | 5 | 5 |
|---|---|---|---|
| P | 1 | 2 | 3 |
| N | 0 | 1 | 2 |

And the old partial-BWTs are:
B[0]: CCT
B[1]: A
B[2]: AT
B[3]: empty
B[4]: empty
B[5]: TCC
By reading the following vector of triples (Q, P, N):

| Q | 1 | 5 | 5 |
|---|---|---|---|
| P | 1 | 2 | 3 |
| N | 0 | 1 | 2 |

It is known that:
  The character of the sequence 0 has been inserted in the position 1 of the partial BWT 1
  The character of the sequence 1 has been inserted in the position 2 of the partial BWT 5
  The character of the sequence 2 has been inserted in the position 3 of the partial BWT 5
The values in the vector of the triples and updated:

| Q | 1 | 2 | 2 |
|---|---|---|---|
| P | 1 | 3 | 4 |
| N | 0 | 1 | 2 |

After sorting, the vectors are:

| Q | 1 | 2 | 2 |
|---|---|---|---|
| P | 1 | 3 | 4 |
| N | 0 | 1 | 2 |

Which can be interpreted as:
  The character of the sequence 0 (that is the symbol C) is to be inserted in the position 1 of the partial BWT 1
  The character of the sequence 1 (that is the symbol G) is to be inserted in the position 3 of the partial BWT 2
  The character of the sequence 2 (that is the symbol G) is to be inserted in the position 4 of the partial BWT 2
The new partial-BWTs are built by inserting the characters as determined:
B[0]: CCT
B[1]: CA
B[2]: ATGG
B[3]: empty
B[4]: empty
B[5]: TCC
Iteration j=4
The characters in position 2 are now considered, so CAC.
The vector of the triples are:

| Q | 1 | 2 | 2 |
|---|---|---|---|
| P | 1 | 3 | 4 |
| N | 0 | 1 | 2 |

The old partial-BWTs are:
B[0]: CCT
B[1]: CA
B[2]: ATGG
B[3]: empty
B[4]: empty
B[5]: TCC
By reading the following vector of triples (Q, P, N):

| Q | 1 | 2 | 2 |
|---|---|---|---|
| P | 1 | 3 | 4 |
| N | 0 | 1 | 2 |

It is known that:
  The character of the sequence 0 has been inserted in the position 1 of the partial BWT 1
  The character of the sequence 1 has been inserted in the position 3 of the partial BWT2
  The character of the sequence 2 has been inserted in the position 4 of the partial BWT2
The values in the vector of the triples are updated:

| Q | 2 | 3 | 3 |
|---|---|---|---|
| P | 3 | 1 | 2 |
| N | 0 | 1 | 2 |

After sorting the vectors are:

| Q | 2 | 3 | 3 |
|---|---|---|---|
| P | 3 | 1 | 2 |
| N | 0 | 1 | 2 |

Which can be interpreted as:
  The character of the sequence 0 (that is the symbol C) is to be inserted in the position 3 of the partial BWT 2
  The character of the sequence 1 (that is the symbol A) is to be inserted in the position 1 of the partial BWT 3
  The character of the sequence 2 (that is the symbol C) is to be inserted in the position 2 of the partial BWT 3
The new partial-BWTs are built by inserting the characters as determined:
B[0]: CCT
B[1]: CA
B[2]: ATCGG B[3]: AC
B[4]: empty
B[5]: TCC
Iteration j=5
The characters in position 1 are now considered, so AAT.
The vector of the triples is:

| Q | 2 | 3 | 3 |
|---|---|---|---|
| P | 3 | 1 | 2 |
| N | 0 | 1 | 2 |

The old partial-BWTs are:
B[0]: CCT
B[1]: CA
B[2]: ATCGG
B[3]: AC
B[4]: empty
B[5]: TCC
By reading the following vector of triples (Q, P, N):

| Q | 2 | 3 | 3 |
|---|---|---|---|
| P | 3 | 1 | 2 |
| N | 0 | 1 | 2 |

It is known that:
 The character of the sequence 0 has been inserted in the position 3 of the partial BWT 2
 The character of the sequence 1 has been inserted in the position 1 of the partial BWT 3
 The character of the sequence 2 has been inserted in the position 2 of the partial BWT 3
The values in the vector of the triples are updated:

| Q | 2 | 1 | 2 |
|---|---|---|---|
| P | 4 | 3 | 5 |
| N | 0 | 1 | 2 |

After sorting the vectors are:

| Q | 1 | 2 | 2 |
|---|---|---|---|
| P | 3 | 4 | 5 |
| N | 1 | 0 | 2 |

It is observed that, in this case, the sorting has changed the vector of the triples. The new characters being considered in this iteration are:
The new character of the sequence 0: A
The new character of the sequence 1: A
The new character of the sequence 2: T
In this iteration, the vectors are interpreted in this way:
 The character of the sequence 1 (that is the symbol A) is to be inserted in the position 3 of the partial BWT 1
 The character of the sequence 0 (that is the symbol A) is to be inserted in the position 4 of the partial BWT 2
 The character of the sequence 2 (that is the symbol T) is to be inserted in the position 5 of the partial BWT 2
The new partial-BWTs are build by inserting the characters as determined:
B[0]: CCT
B[1]: CAA
B[2]: ATCATGG
B[3]: AC
B[4]: empty
B[5]: TCC
Iteration j=6
The characters in position 0 are now considered, so TAG
The vector of the triples is:

| Q | 1 | 2 | 2 |
|---|---|---|---|
| P | 3 | 4 | 5 |
| N | 1 | 0 | 2 |

The old partial-BWTs are:
B[0]: CCT
B[1]: CAA
B[2]: ATCATGG
B[3]: AC
B[4]: empty
B[5]: TCC
By reading the following vector of triples (Q, P, N):

| Q | 1 | 2 | 2 |
|---|---|---|---|
| P | 3 | 4 | 5 |
| N | 1 | 0 | 2 |

It is known that:
 The character of the sequence 1 has been inserted in the position 3 of the partial BWT 1
 The character of the sequence 0 has been inserted in the position 4 of the partial BWT2
 The character of the sequence 2 has been inserted in the position 5 of the partial BWT2
The values in the vector of the triples and updated:

| Q | 1 | 1 | 5 |
|---|---|---|---|
| P | 2 | 4 | 3 |
| N | 1 | 0 | 2 |

After sorting, the vectors are:

| Q | 1 | 1 | 5 |
|---|---|---|---|
| P | 2 | 4 | 3 |
| N | 1 | 0 | 2 |

Recall that the new characters as position 0 are:
The new character of the sequence 0: T
The new character of the sequence 1: A
The new character of the sequence 2: G
Which can be interpreted as:
 The character of the sequence 1 (that is the symbol A) is to be inserted in the position 2 of the partial BWT 1
 The character of the sequence 0 (that is the symbol T) is to be inserted in the position 4 of the partial BWT 1
 The character of the sequence 2 (that is the symbol G) is to be inserted in the position 3 of the partial BWT 5
The new partial-BWTs are built by inserting the characters as determined:
B[0]: CCT
B[1]: CAATA B[2]: ATCATGG
B[3]: AC
B[4]: empty
B[5]: TCGC
Iteration j=7
The symbols $ is position 7 are now considered, as they are all equal then $$$ ($1=$2=$3)
The vector of the triples is:

| Q | 1 | 1 | 5 |
| P | 2 | 4 | 3 |
| N | 1 | 0 | 2 |

The old partial-BWTs are:
B[1]: CAATA
B[2]: ATCATGG
B[3]: AC
B[4]: empty
B[5]: TCGC
By reading the following vector of triples (Q, P, N):

| Q | 1 | 1 | 5 |
| P | 2 | 4 | 3 |
| N | 1 | 0 | 2 |

It is known that know that:
 The character of the sequence 1 (that is the symbol A) has been inserted in the position 2 of the partial BWT 1
 The character of the sequence 0 (that is the symbol T) has been inserted in the position 4 of the partial BWT 1
 The character of the sequence 2 (that is the symbol G) has been inserted in the position 3 of the partial BWT 5
The values in the vector of the triples are updated:

| Q | 1 | 5 | 3 |
| P | 1 | 2 | 3 |
| N | 1 | 0 | 2 |

After sorting, the vectors are:

| Q | 1 | 3 | 5 |
| P | 1 | 3 | 2 |
| N | 1 | 2 | 0 |

Which can be interpreted as:
 The symbol of the sequence 1 (that is the symbol $) is to be inserted in the position 1 of the partial BWT 1
 The symbol of the sequence 3 (that is the symbol $) is to be inserted in the position 2 of the partial BWT 3
 The symbol of the sequence 2 (that is the symbol $) is to be inserted in the position 1 of the partial BWT 5
The new partial-BWTs are built by inserting the symbols as determined:
B[0]: CCT
B[1]: $CAATA
B[2]: ATCATGG
B[3]: AC$
B[4]: empty
B[5]: T$CGC Finally, the concatenation of the partial BWTs is determined:
CCT$CAATAATCATGGAC$T$CGC
In considering the sequences again:

| SeqId | 0 | 1 | 2 | 3 | 4 | 5 | 6 | 7 |
|---|---|---|---|---|---|---|---|---|
| 0 | T | A | C | C | A | A | C | $1 |
| 1 | A | A | A | G | C | T | C | $2 |
| 2 | G | T | C | G | C | T | T | $3 |

If after the iteration j=1, the symbols $ (one for each sequence) are inserted, the BWT of the following suffixes is built:

| SeqId | 6 | 7 |
|---|---|---|
| 0 | C | $1 |
| 1 | C | $2 |
| 2 | T | $3 |

If after the iteration j=2, the symbols $ (one for each sequence) are merged, the BWT of the following suffixes is built:

| SeqId | 5 | 6 | 7 |
|---|---|---|---|
| 0 | A | C | $1 |
| 1 | T | C | $2 |
| 2 | T | T | $3 |

If after the iteration j=3, the symbols $ (one for each sequence) are merged, the BWT of the following suffixes is built:

| SeqId | 4 | 5 | 6 | 7 |
|---|---|---|---|---|
| 0 | A | A | C | $1 |
| 1 | C | T | C | $2 |
| 2 | C | T | T | $3 |

If after the iteration j=4, the symbols $ (one for each sequence) are merged, the BWT of the following suffixes is built:

| SeqId | 3 | 4 | 5 | 6 | 7 |
|---|---|---|---|---|---|
| 0 | C | A | A | C | $1 |
| 1 | G | C | T | C | $2 |
| 2 | G | C | T | T | $3 |

If after the iteration j=5, the symbols $ (one for each sequence) are merged, the BWT of the following suffixes is built:

| SeqId | 2 | 3 | 4 | 5 | 6 | 7 |
|---|---|---|---|---|---|---|
| 0 | C | C | A | A | C | $1 |
| 1 | A | G | C | T | C | $2 |
| 2 | C | G | C | T | T | $3 |

If after the iteration j=6, the symbols $ (one for each sequence) are merged, the BWT of the following suffixes is built:

| SeqId | 1 | 2 | 3 | 4 | 5 | 6 | 7 |
|---|---|---|---|---|---|---|---|
| 0 | A | C | C | A | A | C | $1 |
| 1 | A | A | G | C | T | C | $2 |
| 2 | T | C | G | C | T | T | $3 |

If after the iteration j=7, symbols $ (one for each sequence) is merged, the BWT of the following suffixes is built:

| SeqId | 0 | 1 | 2 | 3 | 4 | 5 | 6 | 7 |
|---|---|---|---|---|---|---|---|---|
| 0 | T | A | C | C | A | A | C | $1 |
| 1 | A | A | A | G | C | T | C | $2 |
| 2 | G | T | C | G | C | T | T | $3 |

Example 2

Computational Experiments

The computational methods as described herein were tested on subsets of a collection of one billion human DNA sequences, each on 100 bases long reads, sequenced from a well-studied African male individual (Bentley et al., 2008, Nature 456:53-59; available from the Sequence Read Archive at the National Center for Biotechnology Information http://trace.ncbi.nlm.nih.gov/Traces/sra/sra.cgi? using the accession number ERA015743). To demonstrate the low resource needs of the algorithms, all tests were carried out on one of two identical instruments, each having 16 Gbytes memory and two Intel Xeon X5450 (Quad-core) 3 GHz processors (only one processor was used for the demonstrations). Each instrument was directly connected to its own array of 146 Gbytes SAS disks in RAID6 configuration, each array having a Hewlett-Packard P6000 RAID controller with 512 Mbytes cache.

Prototypical implementations were developed for Algorithm1 and Algorithm2. For smaller input instances, Algorithm1 and Algorithm2 algorithms were compared to bwte from the bwtdisk toolkit (version 0.9.0; available at http://people.unipmn.it/manzini/bwtdisk/). Bwte implements the blockwise BWT construction algorithm as described in Ferragina et al., 2010. Since bwte constructs the BWT of a single string, string collections were concatenated into this form using 0 as a delimiter; choosing 0 because it is lexicographically smaller than any A, C, G, T, or N. An entirely like-for-like comparison would use a different end marker for each string; however the bwte implementation does not support the many millions of distinct end marker symbols this would require.

The BWT takes more work to compute for string of size km than for a collection of m strings of length k, since the number of symbol comparisons needed to decide the order of two suffixes is not bounded by k. In this particular case, however, the periodic nature of the concatenated string means that 99 out of 100 suffix/suffix comparisons will still terminate within 100 symbols, as one suffix will hit 0 but the other will not, the only exception being the case where both suffixes start at the same position in different strings. The bwte was run using 4 Gbytes of memory, the maximum amount of memory the program allowed to specify.

A compressed suffix array (CSA) on smaller instances was constructed using Siren's program rlcsa (available at http://www.cs.helsinki.fi/group/suds/rlcsa/rlcsa.tgz). On those input instances rlcsa poses an interesting alternative, especially since this algorithm is geared towards indexing text collections as well. The input data was split into 10 batches, a separate index was constructed for each batch and the indexes were merged. With increasing data volumes, however, the computational requirements for constructing the CSA becomes prohibitive on the testing environment. In Siren 2009, 8 threads and up to 36-37 Gbytes of memory are used to construct the CSA of a text collection 41.48 Gbytes in size, although the author describes other variants of the algorithm that would use less RAM than this.

Input strings were generated on an Illumina Genome Analyzer IIx Sequencer, all reads being 100 bp long. The first two instance sizes (43M and 85M) were chosen as data sets comparable to those tested in Ferragina, et al., 2010. Size is the input size in gigabytes, wall clock time (i.e., the amount of time that elapsed from the start to the completion of the instance) is given as microseconds per input base and memory denotes the maximal amount of memory (in Gbytes) used during execution. Algorithm2 and algorithm3 store only a constant and, for the DNA alphabet, negligibly small number of integers in RAM regardless of the size of the input data. The efficiency column reports the CPU efficiency values, the proportion of time for which the CPU was occupied and not waiting for I/O operations to finish, as taken from the output of the /usr/bin/time command. Some of the tests were repeated on a solid-state hard drive (SSD).

Table 1 reports exemplary results for input instances that were generated (BCR=algorithm1, BCRext=algorithm2 and BCRext++=algorithm3). The first two instances, 0043M and 0085M, were sized to match the largest datasets considered in Ferragina et al., 2010. The latter three instances were created to demonstrate the effectiveness of the disclosed computational methods on very large data string collections. Rlcsa and bwte show efficiency (defined as user CPU time plus system CPU time as a fraction of wall clock time) approaching 100% in the smaller data sets (on test instruments and other servers). Even though algorithm1 and algorithm2 exhibit a decrease in efficiency for large datasets, they are both able to process the large 100M dataset at a rate that exceeds the performance of bwte on the 0085M dataset, which is less than one tenth of the size. This efficiency loss, which is contemplated to be due to the internal cache of the disk controller becoming saturated, starts to manifest on smaller datasets for algorithm2 more so than for algorithm1, which is likely to be a consequence of the greater I/O (i.e., input/output) demands of algorithm2. Since the I/O of algorithm2 is dominated by the repeated copying of the input sequences during the radix sort, algorithm2 was modified to minimize the data read to and from the disk during this experiment. For all tests, the best wall clock time achieved is marked in bold, for example 0043M/BCRext++/0.93, 0085M/BCRext++/0.95, 0100M/BCR/1.05, 0800M/BCR/2.25, 1000M/BCR/3.17, 0085M (SSD)/BCR/0.58 and 1000M (SSD)/BCR/0.98.

TABLE 1

| instance | size | program | wall clock | efficiency | memory |
|---|---|---|---|---|---|
| 0043M | 4.00 | bwte | 5.00 | 0.99 | 4.00 |
| | 4.00 | rlcsa | 2.21 | 0.99 | 7.10 |
| | 4.00 | BCR | 0.99 | 0.84 | 0.57 |
| | 4.00 | BCRext | 2.15 | 0.58 | — |
| | 4.00 | BCRext++ | 0.93 | 0.66 | — |

TABLE 1-continued

| instance | size | program | wall clock | efficiency | memory |
|---|---|---|---|---|---|
| 0085M | 8.00 | bwte | 7.99 | 0.99 | 4.00 |
| | 8.00 | rlcsa | 2.44 | 0.99 | 13.40 |
| | 8.00 | BCR | 1.01 | 0.83 | 1.10 |
| | 8.00 | BCRext | 4.75 | 0.27 | — |
| | 8.00 | BCRext++ | 0.95 | 0.69 | — |
| 0100M | 9.31 | BCR | 1.05 | 0.81 | 1.35 |
| | 9.31 | BCRext | 4.6 | 0.28 | — |
| | 9.31 | BCRext++ | 1.16 | 0.61 | — |
| 0800M | 74.51 | BCR | 2.25 | 0.46 | 10.40 |
| | 74.51 | BCRext | 5.61 | 0.22 | — |
| | 74.51 | BCRext++ | 2.85 | 0.29 | — |
| 1000M | 93.13 | BCR | 5.74 | 0.19 | 13.00 |
| | 93.13 | BCRext | 5.89 | 0.21 | — |
| | 93.13 | BCRext++ | 3.17 | 0.26 | — |
| 0085M (SSD) | 8.00 | bwte | 8.11 | 0.99 | 4.00 |
| | 8.00 | rlcsa | 2.48 | 0.99 | 13.40 |
| | 8.00 | BCR | 0.78 | 0.99 | 1.10 |
| | 8.00 | BCRext | 0.89 | 0.99 | — |
| | 8.00 | BCRext++ | 0.58 | 0.99 | — |
| 1000M (SSD) | 93.13 | BCR | 0.98 | 0.91 | 13.00 |
| | 93.13 | BCRext++ | 1.24 | 0.64 | — |

In initial experiments with a zlib library (available at http://ww.zlib.net), the CPU overhead of on-the-fly compression and decompression of the input sequences to and from gzip format more than outweighed any possible efficiency gain that could arise from the reduced file sizes. Additional success was achieved by using a 4-bits-per-base encoding and by observing that, during a given iteration, the entire input sequences were not copied but only the prefixes that still remained to be sorted in future iterations. The resulting new version algorithm3 was otherwise identical to algorithm2 but reduced the processing time for the 1 billion read dataset by 47%, with even greater gains on the smaller datasets.

To see how performance scaled with respect to sequence length, pairs of sequences were concatenated from a collection of 100 million 100-mers to create a set of 50 million 200-mers. While this collection contained the same number of bases, algorithm2 and algorithm3 both took a similar proportion of additional time to create the BWT (69% and 67% respectively), whereas the time needed by algorithm1 was only 29% more than was required for the original collection. It is contemplated that this difference is time efficiency among algorithm1, algorithm2 and algorithm3 was due to the radix sort performed by algorithm2 and algorithm3 requiring twice as much I/O for the 200-mer dataset than for the original collection.

To further investigate the relationship between disk hardware and efficiency, experiments were performed on an instrument whose CPU was identical to those used in previous tests except for the addition of a solid state hard drive (SSD) from OCZ Technology R2 p88 Z-Drive with 1 Tbyte capacity and a reported maximum data transfer rate of 1.4 Gbytes/second. Since both rlcsa and bwte already operated at close to maximum efficiency, it would not be expected that the run time of these programs would benefit from the faster disk access speed of the SSD and their performance when the 0085M dataset was stored on the SSD was in line with this expectation. However, the SSD greatly improved the efficiency of the disclosed algorithms, reducing the run times of algorithm2 and algorithm3 on the 1000M dataset by more than 5-fold and 2-fold respectively, meaning that the BWT of 1 billion 100-mers was created in just over 27 hours using algorithm1, or 34.5 hours with algorithm3.

Example 3

Application of a Reordering Strategy to *E. coli* Sequence Data Compression

Sequencing reads from the *E. coli* strain K12 genome were simulated for use in assessing the effects of sequence coverage, read length and sequencing error on the levels of compression achieved. A 60× coverage of error-free, 100 base reads was sub-sampled into datasets as small as 10× coverage. Compression strategies were compared to determine the efficacy of the RLO and SAP sorting strategies.

FIG. 5 shows a summary plot of the compression ratios (bits per base) at various levels of coverage (10 to 60×) for compression both on the original raw input sequences and the BWT transformed reads. In FIG. 2, Gzip, Bzip2, PPMd (default) and PPMD (large) show compression achieved on the raw sequence data. It was previously determined that the PPMd mode (-m0=PPMd) of 7-Zip was a good choice of second-stage compressor for the BWT strings, as such BWT, BWT-SAP and BWT-RLO report compression results on the BWT using PPMd (default) as the second-stage compressor. As seen in FIG. 5, RLO sorting of the datasets resulted in a BWT that was slightly more compressible than the SAP permuted BWT, however the difference was minimal at 0.36 bpb versus 0.38 bpb at 60×. Both the RLO and SAP strategies resulted in higher compression compared to the compressed BWT of the non-resorted reads at 0.55 bpb. When the Gzip, Bzip2 and PPMd (default) were applied to the original reads, each resulted in a compression level that was not only consistent across all levels of coverage, but also none was able to compress the data below 2 bpb. However, a sweep of the PPMd (default) parameter field yielded a combination (mo=16-mmem=2048 m) that attained a 0.50 bpb compression on the 60× dataset; this parameter setting is the PPMd (large) strategy. It is contemplated that the PPMd (large) compression strategy is possible because the *E. coli* genome is small enough to permit several fold redundancy of the genome to be captured in the 2 Gbytes of working space that this combination specifies.

However, for much larger genomes such as eukaryotic genomes (e.g., humans, etc) this advantage disappears. For example, Table 2 summarizes the results from a set of 192 million human sequence reads (http://www.ebi.ac.uk/ena/data/view/SRX001540) previously analyzed by Yanovsky (2011, Alg Mol Biol 6:23, incorporated herein by reference in its entirety). Different combinations of first-stage (BWT, SAP-permuted BWT) and second-stage (Bzip2 with default parameters, PPMd mode of 7-Zip with default parameters, PPMd mode of 7-Zip with -mo=16-mmem=2048 m deflate mode of 7-Zip with -mx9) compression were compared on the 192 human reads. Time is in CPU seconds as measured on a single core of an Intel Xeon X5450 (Quad-core) 3 GHz processor and compression is in bits per base. As seen in Table 2, when dealing with a large human genome PPMd (large) compresses the BWT of the reads less well than PPMd (Default) as well as being several times slower. Indeed, the SAP strategy resulted in compression times of 1.21 bpb in just over an hour compared to 1.34 bpb in over 14 hours by (i.e., ReCoil method).

TABLE 2

| Method | | Time | | |
| --- | --- | --- | --- | --- |
| Stage 1 | Stage 2 | Stage 1 | Stage 2 | Compression |
| Reads | Bzip2 | N/A | 905 | 2.25 |
|  | PPMd (default) |  | 324 | 2.04 |
|  | PMd (large) |  | 5155 | 2 |
|  | "-mx9" |  | 17974 | 1.98 |
| BWT | Bzip2 | 3520 | 818 | 2.09 |
|  | PPMd (default) |  | 353 | 1.93 |
|  | PPMd (large) |  | 4953 | 2.05 |
|  | "-mx9" |  | 16709 | 2.09 |
| BWT-SAP | Bzip2 | 3520 | 601 | 1.4 |
|  | PPMd (default) |  | 347 | 1.21 |
|  | PPMd (large) |  | 3116 | 1.28 |
|  | "-mx9" |  | 11204 | 1.34 |

The effect of sequencing errors on compression ratios was investigated by simulating 40× sequence coverage data sets of 100 bp reads with different rates of uniformly distributed substitution errors. It was found that an error rate of 1.2% approximately doubled the size of the compressed BWT to 0.90 bpb compared with 0.47 bpb for error-free data at the same coverage.

The effect of read lengths on compression ratios was investigated. A simulated *E. coli* error-free 40× coverage sequence, variable read length data set was evaluated using BWT based compression strategies. It was determined that as the read length increased from 50 bp to 800 bp the size of the compressed BWTs decreased from 0.54 bpb to 0.32 bpb. It is contemplated that longer reads allow for repetitive sequences to be grouped together, which could otherwise potentially be disrupted by suffixed of homologous sequences thereby resulting in an increase in compression with increased sequence read length.

Example 4

Application of a Reordering Strategy to Human Genome Data Compression

Additionally, the performance of the compressor strategies was evalutated using a typical human genome resequencing experiment. The human genome evaluated contained 135.3 Gbp of 100 base pair reads for about 45× coverage of the human genome (http://www.ebi.ac.uk/ena/data/view/ERA015743). In addition to the set of reads (untrimmed reads), a second dataset was created by trimming the reads (trimmed reads) based on their associated quality scores according to the scheme described by bwa (Li and Durbin, 2009). Setting a quality score of 15 (QS=15) as the threshold removed or trimmed approximately 1.3% of the input bases resulting in 133.6 Gbp trimmed data set. The data sets were constructed in RLO and SAP order. Different combinations of first-stage BWT, BWT-RLO and BWT-SAP and second-stage PPMd compression methods were compared on the human data set to provide bits per input base compression statistics. Table 3 demonstrates the improvement in terms of compression after trimming, whereby trimming improved the compression ratio by about 4.5%, or compressed the entire 133.6 Gbp data set down to 7.7 Gbytes of storage space compared to untrimmed compression of 135.3 Gbp down to 8.2 Gbytes of storage space. This is 4 times smaller than the size achieved by a standard Bzip2 compressor on untrimmed reads which demonstrates the large advantage of the disclosed novel strategies in facilitating the building of compressed full text indexes on large scale DNA sequence collections.

TABLE 3

|  | Input size (Gbp) | BWT | BWT-RLO | BWT-SAP |
| --- | --- | --- | --- | --- |
| untrimmed | 135.3 | 0.746 | 0.528 | 0.484 |
| trimmed | 133.6 | 0.721 | 0.504 | 0.462 |

The data demonstrates that reordering the strings in a collection when compressing data provides for better compression over not reordering the strings in a collection. One situation where reordering data for better compression might be problematic is for paired end sequencing reads (e.g., where different ends of a library of DNA templates are sequenced from different ends). However, this situation could be overcome by storing the two reads in a pair at adjacent positions in S (e.g., the first two reads in the collection are reads 1 and 2 of the first read pairs, etc.). The paired information could then be retained after a change in ordering.

In addition, a pointer or other identifier could be associated with each read and its mate to retain the original data order. The algorithms disclosed herein provide for inverting the BWT and recovering the original reads. However, when augmented with relatively small additional data structures the compressed BWT forms the core of the FM-index that allows "count" (e.g., how many times does a k-mer occur in the dataset?) and "locate" (e.g., at what positions in the collection does the k-mer occur?) queries. Several variants of the algorithmic scheme exist which make different tradeoffs between the compression achieved and the time needed for the "count" and "locate" operations. For instance, Ferragina et al (2007) describes a variant of the FM-index that indexes a string T of length n within $nH_k(T)+o(n)$ bits of storage, wherein $H_k(T)$ is the k-th order empirical entropy of T. This index counts the occurrences in T of a string of length p in O(p) time and it locates each occurrence of the query string in $O(\log^{1+E} n)$ time, for any constant $0<\epsilon<1$.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A computer implemented method for determining the sequence of a nucleic acid comprising:
  a) receiving, using a processor, a collection of data strings of nucleic acid sequence data from a nucleic acid sequence dataset wherein said data strings comprise a plurality of characters,
  b) generating, using the processor, a first Burrows Wheeler transform on a first collection of characters of nucleic acid sequence data from the nucleic acid sequence dataset, wherein the first collection of characters comprises a first character from each of said data strings,
  c) merging, using the processor, an untransformed second collection of characters of nucleic acid sequence data from the nucleic acid sequence data set with the first Burrows Wheeler transformed characters to form a merged collection of characters, wherein the untransformed second collection of characters comprises a second character from each of said data strings, d) incrementally building, using the processor, a second Burrows Wheeler transform from the merged first Burrows Wheeler transformed characters and the untransformed second collection of characters, and e) determining, using the processor, the sequence of the nucleic acid based on the incrementally built Burrows Wheeler transform of the nucleic acid.

2. The computer implemented method of claim 1, wherein said nucleic acid sequence comprises DNA or RNA sequences.

3. The computer implemented method of claim 1, wherein said nucleic acid sequence comprises nucleic acid sequences from a plurality of organisms.

4. The computer implemented method of claim 1, wherein said collection of data strings is received from a computer storage medium.

5. The computer implemented method of claim 1, wherein said collection of data strings is received from a computer in real time, wherein steps b) through d) are performed prior to receiving all of the characters of said data strings.

6. The method of claim 1, wherein a collection of data strings is one data string.

7. The computer implemented method of claim 1, wherein a collection of data strings is a plurality of data strings.

8. The computer implemented method of claim 1, wherein said collection of characters are one or more characters from the list comprising A, T, C, G, U and N.

9. The computer implemented method of claim 1, further comprising repeating step d) with at least a third collection of characters from each of said sequence data strings, wherein the third collection of characters comprises a third character from each of said sequence data strings and wherein said third character from each of said sequence data strings is located adjacent to said second character from each of said sequence data strings.

10. The computer implemented method of claim 1, further comprising repeating step d) with at least a third collection of characters from each of said sequence data strings, wherein the third collection of characters comprises a third character from each of said sequence data strings and wherein said third character from each of said sequence data strings is located positionally left of said second character from each of said sequence data strings.

11. The computer implemented method of claim 1, further comprising outputting said determination.

12. The computer implemented method of claim 11, wherein said outputting is to one or more of a graphic user interface, a printer or a computer readable storage medium.

13. The computer implemented method of claim 12, wherein said outputting to a computer readable storage medium is independent of the size of a collection of sequence data sets.

14. The computer implemented method of claim 1, wherein said generating and incrementally building comprises generating and incrementally building the Burrows Wheeler transform on a reordered collection of characters.

15. The computer implemented method of claim 14, wherein said reordered collection of characters is reordered by reverse lexicographic ordering.

16. The computer implemented method of claim 14, wherein said reordered collection of characters is reordered by same as previous ordering.

17. The computer implemented method of claim 14, wherein the reordered collection of characters maximizes compression of the collection of characters compared to a collection of characters that is not reordered.

18. A system for determining the sequence of a nucleic acid of claim 1, comprising:

a) a processor, b) a memory coupled with the processor, the memory storing a plurality of instrument instructions wherein said instructions direct the processor to perform a plurality of logical steps when implemented by the processor, the logical steps comprising:

c) receiving a collection of data strings from a nucleic acid sequence dataset wherein said data strings comprise a nucleic acid sequence, d) generating a Burrows Wheeler transform on a first collection of characters of nucleic acid sequence data from the nucleic acid sequence dataset, wherein the first collection of characters comprises a first character from each of said data strings, e) incrementally merging an untransformed second collection of characters of nucleic acid sequence data from the nucleic acid sequence data set with said first Burrows Wheeler transformed characters, wherein the untransformed second, collection of characters comprises a second character from each of said data strings, thereby building a second Burrows Wheeler transform from the merged first Burrows Wheeler transformed characters and the untransformed second collection of characters, and f) determining the sequence of the nucleic acid from the second Burrows Wheeler transform.

19. The system of claim 18, further comprising outputting the sequence of the nucleic acid.

20. The system of claim 18, wherein said data set comprises nucleic acid sequences from a plurality of organisms.

21. The system of claim 18, wherein said data set is received from a computer storage medium.

22. The system of claim 18, wherein said data set is received from a computer in real time, wherein steps b) through d) are performed prior to receiving all of the characters of said data strings.

23. The system of claim 18, wherein said collection of data strings is one data string.

24. The system of claim 18, wherein said collection of data strings is a plurality of data strings.

25. The system of claim 18, wherein the first character from each of said data strings is adjacent to the respective second character from each of said data strings.

26. The system of claim 18, wherein said first characters from each of said data strings is located positionally right of said second character from each of said data strings, and wherein said merging proceeds in a right to left manner.

27. The system of claim 25, further comprising repeating step d) with at least a third collection of characters from each of said data strings, wherein the third collection of characters comprises a third character from each of said data strings and wherein said third character from each of said data strings is located adjacent to said second character from each of said data strings.

28. The system of claim 26, further comprising repeating step d) with at least a third collection of characters from each of said data strings, wherein the third collection of characters comprises a third character from each of said data strings and wherein said third character from each of said data strings is located positionally left of said second character from each of said data strings.

29. The system of claim 18, further comprising outputting a result of said determination.

30. The system of claim 29, wherein said outputting is to one or more of a graphic user interface, a printer or a computer readable storage medium.

31. The system of claim 18, wherein said outputting to a computer readable medium is independent of the size of the data set.

32. The system of claim 18, further obtaining an untransformed second data set, obtaining a collection of data strings comprising a plurality of characters from said untransformed second data set, merging the collection of strings from said second data set with the collection of strings from the first data set and incrementally building a second BWT thereby determining the BWT from the combined first and second data sets.

33. The system of claim 18, wherein one or more of a collection of datasets is removed from said system between step c) and step e).

34. The system of claim 18, wherein said generating and incrementally building comprises generating and incrementally building the Burrows Wheeler transform on a reordered collection of characters.

35. The system of claim 34, wherein said reordered collection of characters is reordered by reverse lexicographic ordering.

36. The system of claim 34, wherein said reordered collection of characters is reordered by a same as previous ordering.

37. A computer implemented method for maximizing compression of a data set from the Burrows Wheeler transform comprising:
   a) receiving, using a processor, a collection of data strings from a dataset, wherein said data strings comprise a plurality of characters, wherein said dataset is a biopolymer sequence dataset, and wherein said biopolymer sequence data set comprises nucleic acid sequence data,
   b) generating, using the processor, a first Burrows Wheeler transform on a first collection of characters of nucleic acid sequence data from the dataset, wherein the first collection of characters comprises a first character from each of said data strings,
   c) adding, using the processor, a second collection of untransformed characters of nucleic acid sequence data from dataset to said first Burrows Wheeler transformed characters by incrementally merging the untransformed characters from the nucleic acid sequence data with the first Burrows Wheeler transformed characters, thereby generating a second Burrows Wheeler transform, wherein the second collection of characters comprises a second character from each of said data strings.

38. The method of claim 37, wherein said biopolymer sequence data set comprises amino acid sequence data.

39. The computer implemented method of claim 37, wherein said data set comprises nucleic acid sequences from a plurality of organisms.

40. The computer implemented method of claim 37, wherein said data set comprises language text data.

41. The computer implemented method of claim 37, wherein said data set is received from a computer storage medium.

42. The computer implemented method of claim 37, wherein said data set is received from a computer in real time, wherein steps b) through c) are performed prior to receiving all of the characters of said data strings.

43. The method of claim 37, wherein said collection of data strings is one data string.

44. The computer implemented method of claim 37, wherein said collection of data strings is a plurality of data strings.

45. The computer implemented method of claim 37, wherein said collection of characters is from the list comprising nucleotides, and amino acids.

46. The computer implemented method of claim 37, wherein the first character from each of said data strings is adjacent to the respective second character from each of said data strings.

47. The computer implemented method of claim 37, wherein said first characters from each of said data strings is located positionally right of said second character from each of said data strings, and wherein said merging proceeds in a right to left manner.

48. The computer implemented method of claim 46, further comprising repeating step c) with at least a third collection of characters from each of said data strings, wherein the third collection of characters comprises a third character from each of said data strings and wherein said third character from each of said data strings is located adjacent to said second character from each of said data strings.

49. The computer implemented method of claim 47, further comprising repeating step c) with at least a third collection of characters from each of said data strings, wherein the third collection of characters comprises a third character from each of said data strings and wherein said third character from each of said data strings is located positionally left of said second character from each of said data strings.

50. The computer implemented method of claim 37, further comprising outputting a result of said determination.

51. The computer implemented method of claim 50, wherein said outputting is to one or more of a graphic user interface, a printer or a computer readable storage medium.

52. The computer implemented method of claim 51, wherein said outputting to a computer readable medium is independent of the size of the data set.

53. The computer implemented method of claim 37, further receiving a second collection of data strings comprising a plurality of characters from said second data set, merging the collection of strings from said second data set with the collection of strings from the first data set and augmenting the BWT thereby determining the BWT from the combined first and second data sets.

54. The computer implemented method of claim 37, wherein one or more of a collection of datasets is removed from said computer implemented method between step c) and step e).

55. The computer implemented method of claim 37, wherein said generating and augmenting comprises generating and augmenting the Burrows Wheeler transform on a reordered collection of characters.

56. The computer implemented method of claim 55, wherein said reordered collection of characters is reordered by reverse lexicographic ordering.

57. The computer implemented method of claim 56, wherein said reordered collection of characters is reordered by same as previous ordering.

58. A system for determining the Burrows Wheeler transform of a data set of claim 37, comprising:
   a) a processor,
   b) a memory coupled with the processor, the memory storing a plurality of instrument instructions wherein said instructions direct the processor to perform a plurality of logical steps when implemented by the processor, the logical steps comprising:
   c) receiving a collection of data strings from a dataset wherein said data strings comprise a plurality of characters, d) generating a first Burrows Wheeler transform on a first collection of characters of nucleic acid sequence data from the dataset, wherein the first collection of characters comprises a first character from each of said data strings, e) adding an untransformed second collection of characters of nucleic acid sequence data from the dataset with said first Burrows Wheeler transformed collection of characters from the dataset by incrementally merging the untransformed characters second collection of characters with the first Burrows Wheeler transformed collection of characters, thereby generating a second Burrows Wheeler transform, wherein the untransformed second collection of characters comprises a second character from each of said data strings.

59. The system of claim 58, wherein said data set is a biopolymer sequence data set.

60. The system of claim 59, wherein said biopolymer sequence data set comprises nucleic acid sequence data.

61. The system of claim 59, wherein said polymer sequence data set comprises amino acid sequence data.

62. The system of claim 58, wherein said data set comprises nucleic acid sequences from a plurality of organisms.

63. The system of claim 58, wherein said data set comprises language text data.

64. The system of claim 58, wherein said data set is received from a computer storage medium.

65. The system of claim 58, wherein said data set is received from a computer in real time, wherein steps b) through d) are performed prior to receiving all of the characters of said data strings.

66. The system of claim 58, wherein said collection of data strings is one data string.

67. The system of claim 58, wherein said collection of data strings is a plurality of data strings.

68. The system of claim 58, wherein said collection of characters is from the list comprising nucleotides, and amino acids.

69. The system of claim 58, wherein the first character from each of said data strings is adjacent to the respective second character from each of said data strings.

70. The system of claim 58, wherein said first characters from each of said data strings is located positionally right of said second character from each of said data strings, and wherein said merging proceeds in a right to left manner.

71. The system of claim 69, further comprising repeating step d) with at least a third collection of characters from each of said data strings, wherein the third collection of characters comprises a third character from each of said data strings and wherein said third character from each of said data strings is located adjacent to said second character from each of said data strings.

72. The system of claim 70, further comprising repeating step d) with at least a third collection of characters from each of said data strings, wherein the third collection of characters comprises a third character from each of said data strings and wherein said third character from each of said data strings is located positionally left of said second character from each of said data strings.

73. The system of claim 58, further comprising outputting a result of said determination.

74. The system of claim 73, wherein said outputting is to one or more of a graphic user interface, a printer or a computer readable storage medium.

75. The system of claim 74, wherein said outputting to a computer readable medium is independent of the size of the data set.

76. The system of claim 58, further receiving a collection of data strings comprising a plurality of characters from said second data set, merging the collection of strings from said second data set with the collection of strings from the first data set and augmenting the BWT thereby determining the BWT from the combined first and second data sets.

77. The system of claim 58, wherein one or more of a collection of datasets is removed from said system between step c) and step e).

78. The method of claim 58, wherein said generating and augmenting comprises generating and augmenting the Burrows Wheeler transform on a reordered collection of characters.

79. The method of claim 78, wherein said reordered collection of characters is reordered by reverse lexicographic ordering.

80. The method of claim 78, wherein said reordered collection of characters is reordered by same as previous ordering.

* * * * *

UNITED STATES PATENT AND TRADEMARK OFFICE
CERTIFICATE OF CORRECTION

Page 1 of 1

PATENT NO. : 8,798,936 B2
APPLICATION NO. : 13/459968
DATED : August 5, 2014
INVENTOR(S) : Bauer et al.

It is certified that error appears in the above-identified patent and that said Letters Patent is hereby corrected as shown below:

In the Claims

Column 49, Line 4, In Claim 31, delete "claim 18," and insert -- claim 30, --, therefor.

Column 50, Line 54, In Claim 57, delete "claim 56," and insert -- claim 55, --, therefor.

Column 52, Line 33, In Claim 78, delete "method," and insert -- system --, therefor.

Column 52, Line 37, In Claim 79, delete "method," and insert -- system --, therefor.

Column 52, Line 40, In Claim 80, delete "method," and insert -- system --, therefor.

Signed and Sealed this
Twenty-ninth Day of March, 2016

Michelle K. Lee
*Director of the United States Patent and Trademark Office*